(12) United States Patent
Labib et al.

(10) Patent No.: US 8,747,883 B2
(45) Date of Patent: Jun. 10, 2014

(54) MEDICAL ITEM FOR LONG TERM DRUG RELEASE

(75) Inventors: Mohamed E. Labib, Princeton, NJ (US); Theodore Davidson, Princeton, NJ (US); Stanislav S. Dukhin, Goldens Bridge, NY (US); James Christopher Post, Mars, PA (US); Garth Ehrlich, Pittsburgh, PA (US); Paul Stoodley, Chandlers Ford Southampton (GB)

(73) Assignee: Princeton Trade & Technology, Inc., Princeton, NJ (US)

(*) Notice: Subject to any disclaimer, the term of this patent is extended or adjusted under 35 U.S.C. 154(b) by 608 days.

(21) Appl. No.: 12/802,207

(22) Filed: Jun. 2, 2010

(65) Prior Publication Data

US 2011/0300202 A1    Dec. 8, 2011

(51) Int. Cl.
*A61K 9/10*     (2006.01)
*A61P 31/04*    (2006.01)
*A61K 31/496*   (2006.01)

(52) U.S. Cl.
USPC ............... 424/423; 424/78.08; 514/253.08

(58) Field of Classification Search
USPC ............... 424/423, 78.08; 514/253.08
See application file for complete search history.

(56) References Cited

U.S. PATENT DOCUMENTS

| | | | |
|---|---|---|---|
| 4,405,360 A | 9/1983 | Cardarelli | 71/117 |
| 4,863,444 A | 9/1989 | Blömer | 604/304 |
| 5,302,397 A | 4/1994 | Amsden et al. | 424/473 |
| 6,361,526 B1 | 3/2002 | Reisdorf et al. | 604/265 |
| 6,641,831 B1 | 11/2003 | Schierholz | 424/422 |
| 6,723,333 B1 | 4/2004 | Albers et al. | 424/422 |
| 2009/0076480 A1 | 3/2009 | Pudleiner et al. | 604/508 |
| 2009/0171464 A1* | 7/2009 | Imhof | 623/22.21 |
| 2009/0171465 A1* | 7/2009 | Bucay-Couto et al. | 623/23.7 |
| 2009/0263460 A1* | 10/2009 | McDonald | 424/426 |
| 2010/0273864 A1* | 10/2010 | Lichter et al. | 514/44 R |

FOREIGN PATENT DOCUMENTS

WO    WO2009/129439 A2    10/2009    ............ A61L 27/18

OTHER PUBLICATIONS

Sprockel, Internationl Journal of Pharmaceutics, vol. 155 pp. 191-199 (1997).*
Lee et al.,"Overview of Controlled-Release Drug Delivery", P.1-13 in "Controlled—Release Technology", ACS Symposium Series 348 Amer. Chem. Society Washington DC 1987.
Scheirholz et al.. "Controlled Release of Antibiotics From Biomedical Polyurethanes: Morphological and Structural Features", *Biomaterials*, 18 (12), 839-844 (1997).
Sprockel et al., "A Melt Extrusion Process for Manufacturing Matrix Drug Delivery Systems", Int. J. of Pharmaceutics, 191-199 (1997).

* cited by examiner

*Primary Examiner* — Anoop Singh
*Assistant Examiner* — Anna Falkowitz
(74) *Attorney, Agent, or Firm* — Sheldon Kavesh

(57) ABSTRACT

Polymeric articles capable of releasing drugs at therapeutic levels over extended periods of time, and methods for producing the extended release articles.

17 Claims, 11 Drawing Sheets

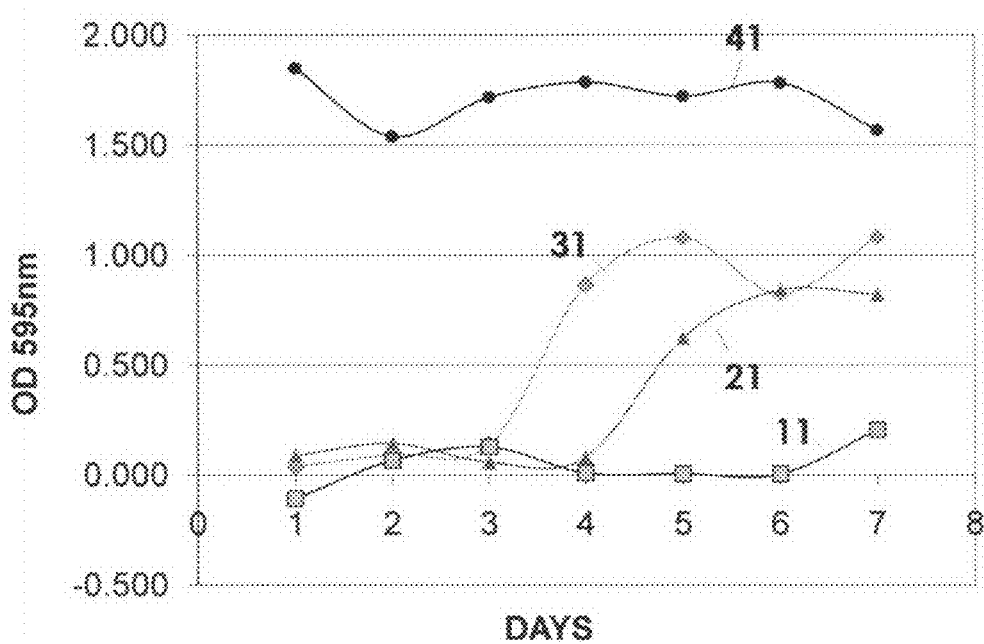

MEDICAL ITEM FOR LONG TERM DRUG RELEASE

BACKGROUND OF THE INVENTION

1. Field of the Invention

The invention relates to polymeric articles capable of releasing drugs at therapeutic levels over extended periods of time, and to methods for producing the extended release articles.

2. Description of the Related Art

An ideal drug delivery system has been suggested to be one which provides the drug only when and where it is needed, and in the minimum dosage required to elicit the desired therapeutic effects. Extended release technology permits delivery to a patient of drug concentrations at therapeutic levels for extended periods without repeated dosage and consequent cycling concentrations.

A great many specific systems for controlled release of drugs from polymers have previously been described. These systems may be broadly classified as follows:
- Bioerodible systems. e.g., WO 2009/129439 A2
- Drug-polymer chemical conjugates
- Membrane-reservoir systems
- Osmotic pumping
- Osmotic rupturing. e.g., U.S. Pat. No. 5,302,397
- Porous polymers
- Polymer erosion
- Polymer swelling
- Diffusion through a matrix This latter approach of diffusion through a matrix has been extensively employed for example in U.S. Pat. Nos. 4,863,444; 6,361,526 B1; 6,641,831 B1; 6,723,333 B1; United States Patent Applications 2009/0076480 A1; 2009/0171465; and in publications such as:

Sprockel et al, "A Melt Extrusion Process For Manufacturing Matrix Drug Delivery Systems", *Int. J. Pharmaceutics*, 155, 191-199 (1997)

Schierholz et al., "Controlled Release of Antibiotics From Biomedical Polyurethanes: Morphological and Structural Features". *Biomaterials*, 18, No. 12, 839-844 (1997)

P. I Lee and W. R. Good, Eds., "Overview of Controlled-Release Drug Delivery" in "Controlled Release Technology", ACS Symposium Series 348, American Chemical Society, Washington, D., 1987

Drug delivery by diffusion through a matrix has been described and criticized as follows:

"Historically, the most popular diffusion-controlled delivery system has been the matrix system, such as tablet and granules, where the drug is uniformly dissolved or dispersed, because of its low cost and ease of fabrication. However, the inherent drawback of the matrix system is its first-order release behavior with continuously diminishing release rate." (emphasized in original)

P. I Lee and W. R. Good, Eds., "Controlled Release Technology", American Chemical Society, Washington, D., P. 5, 1987

The articles of the invention are solid, non-porous composites prepared by uniformly dispersing a bioactive agent in a non-biodegradable thermoplastic polymer melt, then cooling to a non-porous solid state. The composite may be formed into useful articles by standard methods of plastics processing such as extrusion, compression, or injection molding. The drug is released by diffusion through the polymer matrix. The inventive articles have the merits of low cost and ease of fabrication combined with extended drug release and essentially constant drug release rate after an initial induction period. Examples of the inventive articles containing antibiotics have long term antibacterial effect without cytotoxicity to fibroblasts. This surprising combination of properties satisfies long standing, but unmet needs.

SUMMARY OF THE INVENTION

The term "drug" and its equivalent "bioactive agent" as used herein, is herein intended to have its broadest interpretation as any therapeutically, prophylactically beneficial active substance, or mixture thereof, which is delivered to a living organism to produce a desired, usually beneficial effect. In comparison with the prior art, the inventive articles employ a bioactive agent with a particle size distribution best described by a Weibull function and/or the inventive articles are comprised of three phases of the bioactive agent. The invention further comprises a method for preparing polymer composites containing bioactive agents and articles usefully made there from.

In a first embodiment, the invention is a solid, non-porous composite comprised of:

a) A non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 35° C. in 30 days; and b) one or more bioactive agents dispersed uniformly throughout said polymer material; said bioactive agents comprising about 1 to about 60 percent by weight of said polymer plus bioactive agents;

wherein at least one said bioactive agent has less than about 5 percent weight loss at a temperature of 200° C. when measured in a pure state by thermogravimetric analysis at a heating rate of 10°C./min; and, wherein, as measured by a Horiba Instruments, Inc., Model LA-900 Laser Scattering Particle Size Distribution Analyzer before dispersion in said polymer material, at least one said bioactive agent has a particle size distribution best described by a Weibull function with an index of determination of at least about 0.90, said distribution having a characteristic size of from about 5 to about 100 micrometers and a shape factor from about 1.1 to about 5.

In a second embodiment, the invention is a solid, non-porous composite comprised of:

a) a non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 35° C. in 30 days; and b) one or more bioactive agents dispersed uniformly throughout said polymer material; said bioactive agents comprising about 1 to about 60 percent by weight of said polymer plus bioactive agents;

wherein at least one said bioactive agent has less than about 5 percent weight loss at a temperature of 200° C. when measured in a pure state by thermogravimetric analysis at a heating rate of 10° C./min; and, wherein said bioactive agent is present in said polymer material as:

i) a solid solution phase with said polymer material comprised of from about 0.1 to about 30 percent by weight of said bioactive agent; and ii) a solid solution phase with said polymer material comprised of from about 95 to about 99.99 percent by weight of said bioactive agent; and iii) a phase selected from a supersaturated solution, an essentially pure bioactive agent, a solid solution comprised of bioactive agents, and their combination.

In a third embodiment, the invention is a solid, non-porous composite comprised of:

a) a non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 35° C. in 30 days; and b) one or more bioactive agents dispersed uniformly throughout said polymer material; said bioactive agents comprising about 1 to about 60 percent by weight of said polymer plus bioactive agents;

wherein at least one said bioactive agent has less than about 5 percent weight loss at a temperature of 200° C. when measured in a pure state by thermogravimetric analysis at a heating rate of 10° C./min;

wherein, as measured by Horiba Instruments, Inc., Model LA-900 Laser Scattering Particle Size Distribution Analyzer before dispersion in said polymer material, at least one said bioactive agent has a particle size distribution best described by a Weibull function with an index of determination of at least about 0.90, said distribution having a characteristic size of from about 5 to about 100 micrometers and a shape factor from about 1.1 to about 5; and wherein said bioactive agent is present in said polymer material as:

i) a solid solution phase with said polymer material comprised of from about 0.1 to about 30 percent by weight of said bioactive agent; and ii) a solid solution phase with said polymer material comprised of from about 95 to about 99.99 percent by weight of said bioactive agent; and iii) a phase selected from a supersaturated solution, an essentially pure bioactive agent, a solid solution comprised of bioactive agents, and their combination.

In a fourth embodiment, the invention is a method of making a non-porous solid composite comprising the steps of:

a) selecting one or more thermoplastic polymer materials melt-processable at a temperature not exceeding 260° C., wherein said one or more polymer materials are suitable for implantation in a living mammal;

b) optionally granulating said polymer materials to particles of a size that pass through a 0.25 mm sieve opening;

c) fluxing said polymer materials at elevated temperature;

d) selecting one or more solid bioactive agents in powder form, wherein at least one said bioactive agent exhibits a weight loss of less than about 5 percent at a temperature of 200° C. when measured by thermogravimetric analysis at a heating rate of 10° C./min, and wherein, as measured by Horiba Instruments, Inc., Model LA-900 Laser Scattering Particle Size Distribution Analyzer, at least one said bioactive agent has a particle size distribution best described by a Weibull function with an index of determination of at least about 0.90, said distribution having a characteristic size of from about 5 to about 100 micrometers and a shape factor from about 1.1 to about 5.

e) adding said bioactive agent to said fluxed polymer materials and mixing under sufficient shear, time and temperature to form a uniform mixture comprising from about 1 to about 60 percent by weight of said bioactive agents;

f) cooling said mixture to room temperature to form a non-porous solid composite material containing un-dissolved bioactive agent.

The invention also includes an article selected from the group consisting of tympanostomy tubes, central venous catheters, total parenteral nutrition lines, Tenckhoff catheters, and Hickman/Broviak catheters comprising a composite of the invention.

BRIEF DESCRIPTION OF THE DRAWINGS

FIG. 13 is a plot of optical density as a function of time for Example 16.

DETAILED DESCRIPTION OF THE INVENTION

Figure 1:
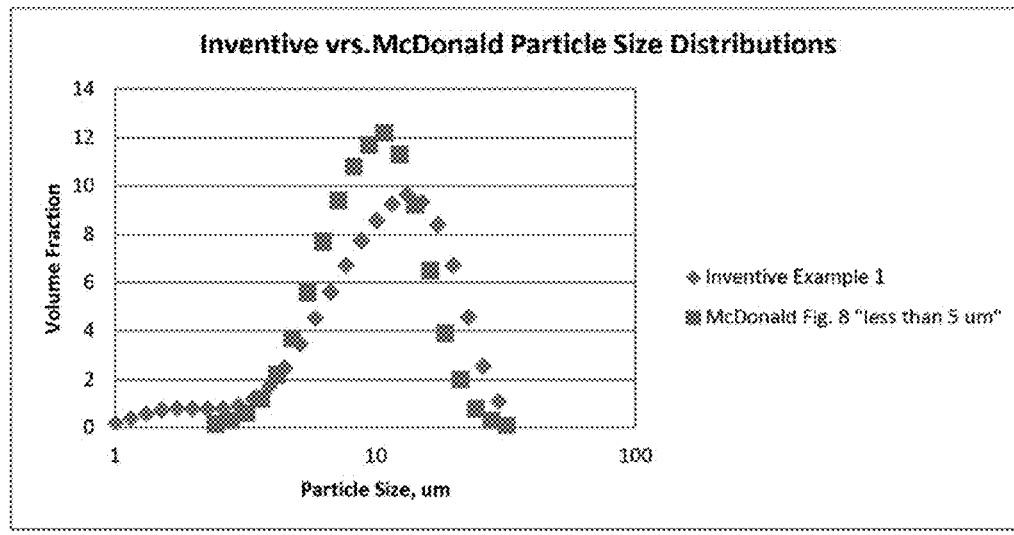
FIG. 1 is a DSC scan of an ethylene-vinyl acetate copolymer containing 18% by weight of vinyl acetate.

In a first embodiment, the invention is a solid, non-porous composite comprised of:

a) a non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 35° C. in 30 days; and b) one or more bioactive agents dispersed uniformly throughout said polymer material; said bioactive agents comprising about 1 to about 60 percent by weight of said polymer plus bioactive agents;

wherein at least one said bioactive agent has less than about 5 percent weight loss at a temperature of 200° C. when measured in a pure state by thermogravimetric analysis at a heating rate of 10° C./min; and, wherein, as measured by a Horiba Instruments, Inc., Model LA-900 Laser Scattering Particle Size Distribution Analyzer before dispersion in said polymer material, at least one said bioactive agent has a particle size distribution best described by a Weibull function with an index of determination of at least about 0.90, said distribution having a characteristic size of from about 5 to about 100 micrometers and a shape factor from about 1.1 to about 5.

In a second embodiment, the invention is a solid, non-porous composite comprised of:
a) a non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 35° C. in 30 days; and
b) one or more bioactive agents dispersed uniformly throughout said polymer material; said bioactive agents comprising about 1 to about 60 percent by weight of said polymer plus bioactive agents;
wherein at least one said bioactive agent has less than about 5 percent weight loss at a temperature of 200° C. when measured in a pure state by thermogravimetric analysis at a heating rate of 10° C./min; and,
wherein said bioactive agent is present in said polymer material as:
i) a solid solution phase with said polymer material comprised of from about 0.1 to about 30 percent by weight of said bioactive agent; and
ii) a solid solution phase with said polymer material comprised of from about 95 to about 99.99 percent by weight of said bioactive agent; and
iii) a phase selected from a supersaturated solution, an essentially pure bioactive agent, a solid solution comprised of bioactive agents, and their combination.

In a third embodiment, the invention is a solid, non-porous composite comprised of:
a) a non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 35° C. in 30 days; and
b) one or more bioactive agents dispersed uniformly throughout said polymer material; said bioactive agents comprising about 1 to about 60 percent by weight of said polymer plus bioactive agents;
wherein at least one said bioactive agent has less than about 5 percent weight loss at a temperature of 200° C. when measured in a pure state by thermogravimetric analysis at a heating rate of 10° C./min;
wherein, as measured by Horiba Instruments, Inc., Model LA-900 Laser Scattering Particle Size Distribution Analyzer before dispersion in said polymer material, at least one said bioactive agent has a particle size distribution best described by a Weibull function with an index of determination of at least about 0.90, said distribution having a characteristic size of from about 5 to about 100 micrometers and a shape factor from about 1.1 to about 5; and wherein said bioactive agent is present in said polymer material as:
i) a solid solution phase with said polymer material comprised of from about 0.1 to about 30 percent by weight of said bioactive agent; and
ii) a solid solution phase with said polymer material comprised of from about 95 to about 99.99 percent by weight of said bioactive agent; and
iii) a phase selected from a supersaturated solution, an essentially pure bioactive agent, a solid solution comprised of bioactive agents, and their combination.

As used herein, "non-biodegradable thermoplastic polymer material" means that devices comprising said polymer material have been approved for implantation in a living mammal by the United States Food and Drug Administration. It is intended, that "non-biodegradable" is to be construed as synonymous with the terms "non-bio-absorbable" and "non-bio-erodible".

Preferably, the thermoplastic polymer material employed in the invention is selected from the group consisting of polyurethanes, polysilicones, polyamides, natural rubber, synthetic elastomers, polyethylene glycol, ethylene-vinyl acetate copolymers, and their blends, and their mixtures.

More preferably, the thermoplastic polymer material is selected from the group consisting of ethylene-vinyl acetate copolymer, polyethylene glycol and their blends and mixtures.

Yet more preferably, the thermoplastic polymer material is selected from the group consisting of an ethylene-vinyl acetate copolymer containing from about 10 to about 50 percent by weight of vinyl acetate, polyethylene glycol having a weight average molecular weight of from about 2,000 to about 20,000 Daltons, and their blends and mixtures.

Most preferably, the thermoplastic polymer material is selected from the group consisting of an ethylene-vinyl acetate copolymer containing from about 15 to about 35 percent by weight of vinyl acetate, polyethylene glycol having a weight average molecular weight of from about 4,000 to about 10,000 Daltons, and their blends and mixtures.

Preferably, a 1.6 mm thick disk of said thermoplastic polymer material has less than about 0.75 percent by weight dissolution in distilled water at 35° C. in 30 days; more preferably, less than about 0.5 percent by weight dissolution, and most preferably, less than about 0.3 percent by weight dissolution.

Preferably, a composite of the invention contains from about 3 to about 30 percent by weight of bioactive agent. More preferably, a composite of the invention contains from about 3 to about 15 percent by weight of bioactive agent.

A composite material of the invention may contain less than about 25 percent by weight of materials commonly used in polymers selected from the group consisting of plasticizers, colorants, anti-oxidant, stabilizers, and fillers. Excipients are not commonly used in polymers and are specifically excluded from a composite of the invention.

The bioactive agents employed in the invention are solids selected from the group consisting antibiotics, anti-inflammatories, bacterial signaling compounds, bacterial signal inhibitors, hormones, anti-sclerotic agents, birth control agents, interferons, insulin, progesterone and their combination.

Preferably, the bioactive agents are antibiotics selected from the group consisting of carbapenems, cephalosporins, penicillins, lincosamides, tetracyclins, macrolides, glycopeptides, quinolones, oxazolidinones, aminoclycosides, gyrase inhibitors, and their combination.

More preferably, the bioactive agents are selected from the group consisting of beta lactam, meropenem, ceftazidime, amoxicillin, clindamycin, tetracycline, erythromycin, vancomycin, ciprofloxacin, linezolid, usnic acid, polyhexamethylene biguanide, N-acetylcysteine, rifampicin, minocycline and their combination.

Most preferably, the bioactive agents are selected from the group consisting of ciprofloxacin, ciprofloxacin hydrochloride, usnic acid, sodium usnate, polyhexamethylene biguanide, polyhexamethylene biguanide hydrochloride and their combination.

Preferably, the bioactive agents employed in the invention have less than about 2.5 percent weight loss at a temperature of 200° C. when measured in a pure state by thermogravimetric analysis at a heating rate of 10° C./min, and more preferably less than about one percent weight loss.

The bioactive agents employed in the invention are solids in powder form. Preferably, at least one bioactive agent has a particle size distribution best described by a Weibull function with an index of determination of at least 0.90, said distribution having a characteristic size of from about 5 to about 100 micrometers and a shape factor from about 1.1 to about 5. Preferably, each of the bioactive agents employed in the invention has a particle size distribution best described by a Weibull function having an index of determination of at least about 0.90, a characteristic size of from about 5 to about 100 micrometers and a shape factor from about 1.1 to about 5. Particle size distributions are measured by a Horiba Instruments, Inc., Model LA-900 Laser Scattering Particle Size Distribution Analyzer.

The expression "a particle size distribution best described by a Weibull function" means that regression of particle sizes against a Weibull function of the particle sizes yields an index of determination that is greater than the index of determination obtained by regression with any one of: a normal distribution, a log normal distribution, an exponential distribution, or an extreme value distribution.

A Weibull distribution of particle sizes is described by the following relationship:

$$F(d) = 1 - e^{-\left(\frac{d}{D}\right)^S} \qquad \text{Eq. 1}$$

where:
d is the particle size, microns
e is the base of natural logarithms, equal to 2.71828 approximately
F(d) is the cumulative size fraction of particles smaller than d
D is a characteristic size for the distribution, microns
S is a shape factor for the distribution, dimensionless For a Weibull particle size distribution, a plot of log(d) versus log [ln (1/(1−F(d)))] is a straight line having a slope of 1/S and having an intercept of log(D). The index of determination is found by regression analysis of log(d) versus log [ln (1/(1−F))]. Preferably, the index of determination is at least about 0.92. More preferably, the index of determination is at least about 0.94, yet more preferably at least about 0.96, and most preferably at least about 0.98.

If a selected bioactive agent powder is not available having a desired Weibull particle size distribution, one can be created from a powder having some other initial particle size distribution. The man of ordinary skill in the art will pass the powder through a series of screens of increasingly finer mesh size, and then combine the collected size fractions in appropriate proportions. Grinding or milling beforehand may be employed to increase the proportion of finer particles, or any one of several agglomeration techniques known in the art may be employed beforehand to increase the proportion of larger particles.

Preferably, a bioactive powder used in the invention has a Weibull particle size distribution with a characteristic size of from about 10 to about 100 micrometers and a shape factor from about 1.2 to about 4. More preferably, the Weibull particle size distribution has a characteristic size of from about 10 to about 75 micrometers and a shape factor from about 1.2 to about 3.5. Most preferably, the Weibull particle size distribution has a characteristic size of from about 10 to 40 micrometers and a shape factor from about 1.3 to about 3.

A composite of the invention containing an antibiotic is useful in a device protective against colonization by organisms selected from the genera consisting of *Corynebacterium, Enterococcus, Escherichia, Haemophilus, Mycoplasma, Neisseria, Pseudomonas, Staphlococcus, Streptococcus, Campylobacter, Propionobacterium, Klebsiella, Enterobacter, Bacillus, Burkholderia, Mycobacterium, Clostridium, Legionella, Listeria, Salmonella, Vibrio, Candida*, and their combination.

A composite of the invention containing an antibiotic is useful in a device selected from the group consisting of tympanostomy tubes, central venous catheters, venous access devices, urinary catheters, dialysis catheters, peripheral IV catheters, ventricular shunts and drains, total parenteral nutrition lines, Tenckhoff catheters, Hickman/Broviak catheters, orthopedic implants, cochlear implants, dental implants, pacemaker leads, sutures, meshes, and stents.

In a fourth embodiment, the invention is a method of making a non-porous solid composite comprising the steps of:
a) selecting one or more thermoplastic polymer materials melt-processable at a temperature not exceeding 260° C., wherein said one or more polymer materials are suitable for implantation in a living mammal;
b) optionally granulating said polymer materials to particles of a size that pass through a 0.25 mm sieve opening;
c) fluxing said polymer materials at elevated temperature;
d) selecting one or more solid bioactive agents in powder form, wherein at least one said bioactive agent exhibits a weight loss of less than about 5 percent at a temperature of 200° C. when measured by thermogravimetric analysis at a heating rate of 10° C./min, and wherein, as measured by Horiba Instruments, Inc., Model LA-900 Laser Scattering Particle Size Distribution Analyzer, at least one said bioactive agent has a particle size distribution described by a Weibull function with an index of determination of at least 0.90, said distribution having a characteristic size of from about to about 100 micrometers and a shape factor from about 1.1 to about 5.
e) adding said bioactive agents to said fluxed polymer materials and mixing under sufficient shear, time and temperature to form a uniform mixture comprising from about 1 to about 60 percent by weight of said bioactive agents;
f) cooling said mixture to room temperature to form a non-porous solid composite material containing un-dissolved bioactive agent.

Preferably, the polymer materials and bioactive agents are selected from those previously described herein.

The formation of a phase structure wherein two solid solution phases of bioactive agent and polymer coexist with un-dissolved bioactive agent requires chemical affinity between the bioactive agent and the polymer. Additionally, it is believed that satisfaction of two necessary but not sufficient process conditions must be met. First, the bioactive agent and polymer must be combined in the polymer melt at elevated temperature, and second, the molten state must be maintained for sufficient time for solutions to form. Preferably, the fluxed polymer and bioactive agents are subject to elevated temperature and shear for at least about 10 minutes, more preferably at least about 15 minutes, and most preferably, at least about 20 minutes.

The invention also includes an article selected from the group consisting of tympanostomy tubes, central venous catheters, total parenteral nutrition lines, Tenckhoff catheters, and Hickman/Broviak catheters comprising a composite of the invention.

EXAMPLES

The following examples are presented to provide a more complete understanding of the invention. The specific techniques, conditions, materials, proportions and reported data set forth to illustrate the principles of the invention are exemplary and should not be construed as limiting the scope of the invention

Example 1

A solid thermoplastic polymer material was selected consisting of an ethylene-vinyl acetate copolymer (hereinafter referred to as an "EVA") containing 18% by weight of vinyl acetate (VA). The EVA from E.I DuPont, designated ELVAX™ 560, had a melt index of 2.5 g/10 minutes as measured by ASTM D 1238. A 1.6 mm thick disk of this EVA had 0.28 percent by weight of dissolution in distilled water at 35° C. in 30 days. The EVA is non-biodegradable. Devices comprised of EVA have been approved by the United States Food and Drug Administration for implantation in a living mammal. A differential scanning calorimetry (DSC) scan of the melting of this EVA at a heating rate of 10° C./min is shown in FIG. 1. The pure EVA melted over a temperature range of 67° C. to 98° C.

Figure 2:
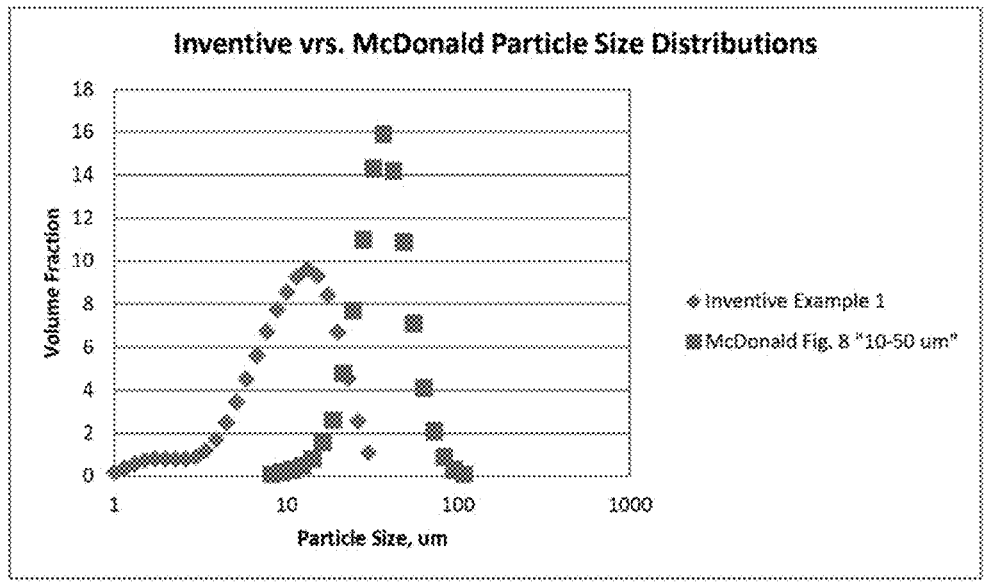
FIG. 2 is a DSC scan of ciprofloxacin.

A bioactive agent was selected consisting of ciprofloxacin betaine powder (C.A.S. Registry No. 85721-33-1). Ciprofloxacin is a broad spectrum antimicrobial agent having less than 1 percent weight loss at a temperature of 250° C. when measured in a pure state by thermogravimetric analysis at a heating rate of 10° C./min. A DSC scan of the melting of this ciprofloxacin powder at a heating rate of 10° C./min is shown in FIG. 2. The ciprofloxacin melted over a temperature range of 252° C. to 271° C.

Figure 3:
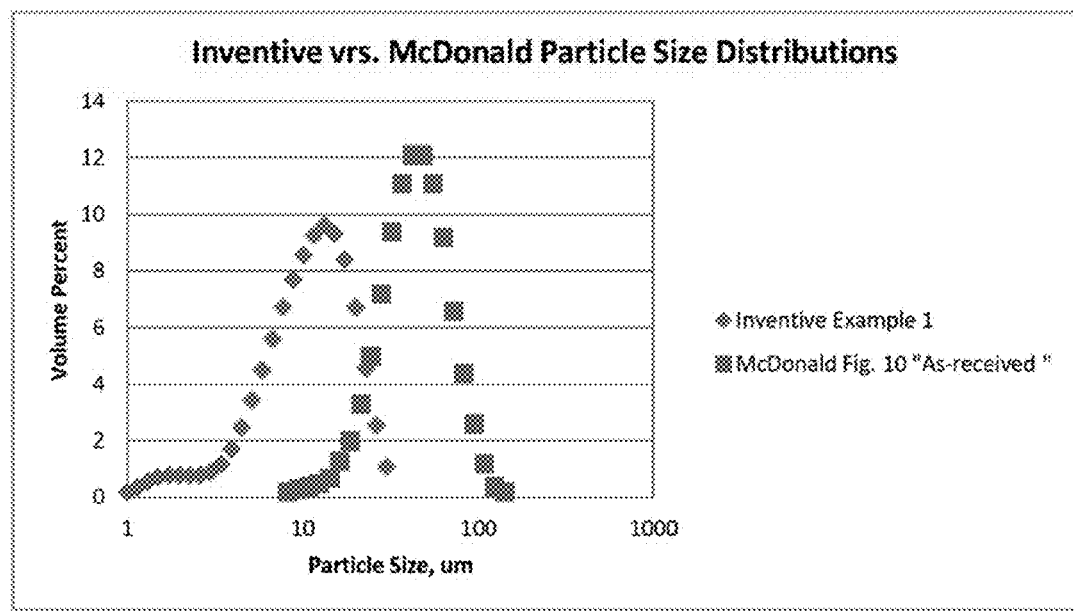
FIG. 3 is a plot of the particle size distributions of the ciprofloaxacin used in the examples.
Figure 4:
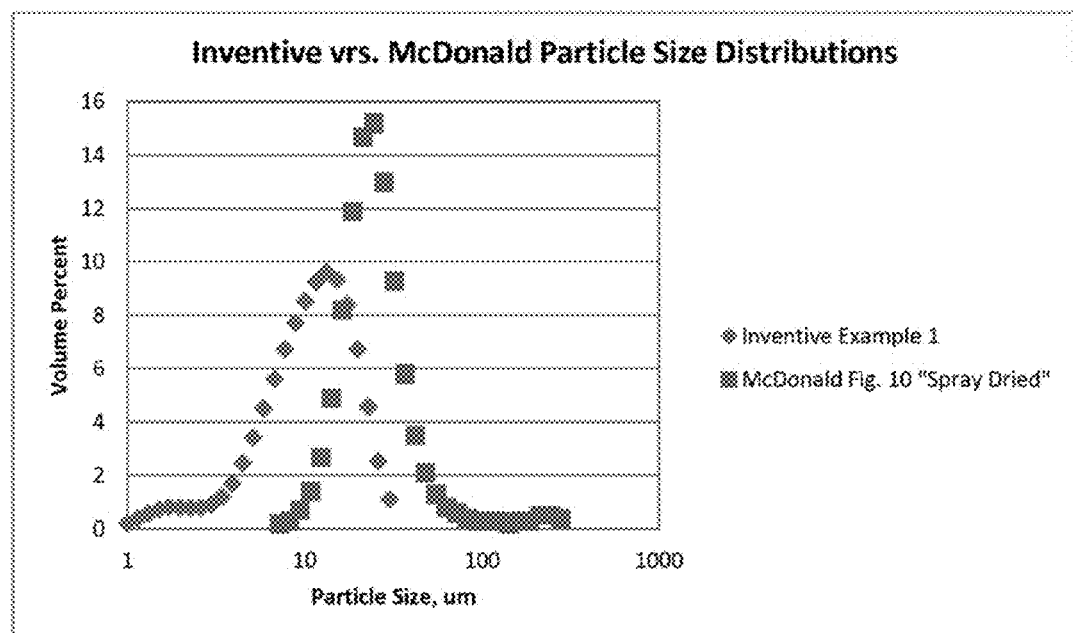
FIG. 4 is a Weibull plot of the particle size distribution of a ciprofloxacin bioactive agent used in the examples of the invention.

The selected ciprofloxacin was further characterized by use of a Horiba Instruments, Inc Model LA-900 Laser Scattering Particle Size Distribution Analyzer. This instrument measures the volume of particles having a size between selected upper and lower limits. The selected ciprofloxacin powder had particle size distribution best described by a Weibull function with an index of determination of 0.991, a characteristic size of 12.25 micrometers, and a shape factor of 2.054 The particle size distribution of the selected ciprofloxacin is given in Table I below, and is plotted as line 10 in FIG. 3. A Weibull plot of this particle size distribution conforming to the invention is shown in FIG. 4.

35 grams of the selected EVA was charged to the mixing chamber of a Brabender Plasticorder preheated to a temperature of 185° C. The mixing chamber of the Brabender Plasticorder was equipped with two sigma-style co-rotating blades and had a capacity of 45 cm³. The EVA was melted at a mixing speed of 35 rpm under a flow of dry nitrogen.

When the EVA had completely melted, 6.176 grams (15.0 percent by weight) of the selected ciprofloxacin powder was added gradually to the mixer. After adding the ciprofloxacin, the speed of the mixer was increased to 60 RPM for 10 minutes to produce a uniform mixture of the ciprofloxacin powder in the EVA copolymer melt.

The mixer was turned off and the ciprofloxacin/EVA mixture was removed from the mixer, transferred to a glass container and cooled to room temperature under ambient conditions to solidify into a solid, non-porous composite material of the invention.

Optical microscopy of this composite material of the invention showed the presence of a dispersed phase of ciprofloxacin particles.

Figure 5:
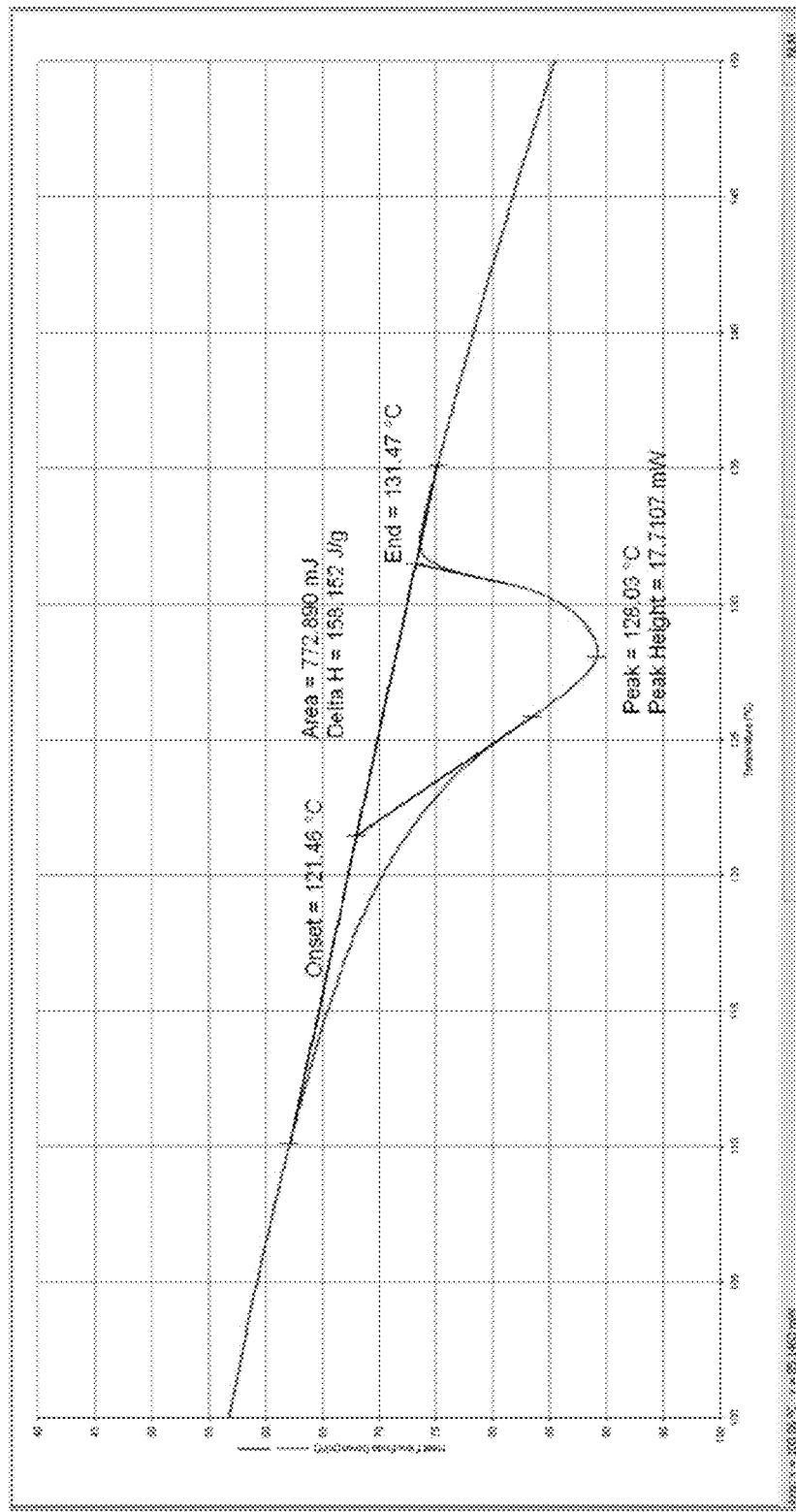
FIG. 5 is a DSC scan of a composite of the invention.

A DSC scan of this composite material of the invention at a heating rate of 10° C./min is shown in FIG. 5. The DSC scan shows melting of the EVA phase over the temperature range of 52° C. to 98° C.: a lower onset and broadening of its melting range compared to the pure EVA. The DSC scan of FIG. 5 also shows melting of the ciprofloxacin phase over the temperature range of 232° C. to 273° C.: again a lower onset and broadening of its melting range compared to the pure ciprofloxacin material. These lower onsets and broadening of the melting ranges of both the EVA and the ciprofloxacin, indicate the presence in the composite of a solid solution phase of ciprofloxacin in EVA, and a solid solution phase of EVA in ciprofloxacin in addition to the un-dissolved ciprofloxacin particles. It is estimated that the solid solution of ciprofloxacin in EVA contained less than about 1 percent by weight of ciprofloxacin, and the solid solution of EVA in ciprofloxacin contained less than about 1 percent by weight of EVA.

Example 2

40 grams of the same EVA containing 18 wt. % vinyl acetate as described in Example 1 was charged to the mixing chamber of the same Brabender Plasticorder as described in Example 1 preheated to a temperature of 185° C. The EVA was melted at a mixing speed of 35 rpm under a flow of dry nitrogen.

When the EVA had completely melted, 1.237 grams (3.00 percent by weight) of the same ciprofloxacin powder as described in Example 1 was added gradually to the mixer. The speed of the mixer was increased to 60 RPM for 10 minutes to produce a uniform dispersion of the ciprofloxacin powder in the EVA melt.

The mixer was turned off and the ciprofloxacin/EVA dispersion was removed from the mixer, transferred to a glass container and cooled to room temperature under ambient conditions to solidify into a solid, non-porous composite material of the invention.

Optical microscopy of this composite material of the invention showed the presence of a dispersed phase of un-dissolved ciprofloxacin particles. DSC determination of the phases present was not done, but it is believed that two solid solution phases of ciprofloxacin/EVA were formed as in Example 1.

Example 3

34.47 grams of the same EVA containing 18 wt. % vinyl acetate described in Example 1 and 5.53 grams of polyethylene glycol (PEG) were charged to the mixing chamber of the same Brabender Plasticorder as described in Example 1 preheated to a temperature of 175° C. The PEG from Sigma-Aldrich had a molecular weight of 8000 Daltons. The EVA copolymer and polyethylene glycol were melted at a mixing speed of 35 rpm under a flow of dry nitrogen.

When the EVA and PEG had completely melted, 2.553 grams (6.00 percent by weight) of the same ciprofloxacin powder as described in Example 1 was added gradually to the mixer. The speed of the mixer was increased to 60 RPM for 10 minutes to produce a uniform dispersion of the ciprofloxacin powder in the EVA and PEG melt.

The mixer was turned off and the ciprofloxacin/polymer dispersion was removed from the mixer, transferred to a glass container and cooled to room temperature under ambient conditions to solidify into solid, non-porous composite material of the invention.

Optical microscopy of this composite material of the invention showed the presence of a dispersed phase of ciprofloxacin particles. While differential scanning calorimetry was not performed on this composite, it is believed that two solid solution phases of ciprofloaxacin/EVA and EVA/ciprofloxacin were present here as in the composite of Example 1.

A control sample was prepared consisting only of the EVA and PEG in the same proportions as above but without any ciprofloxacin. A 1.6 mm thick disk of this material showed less than 1% dissolution in distilled water at 35° C. in 30 days.

Example 4

35 grams of the same EVA copolymer containing 18 wt. % vinyl acetate as described in Example 1 was charged to the mixing chamber of the same Brabender Plasticorder as described in Example 1 preheated to a temperature of 185° C.

The ciprofloxacin betaine powder employed had a particle size distribution best described by a log normal distribution with an index of determination of 0.998 a mean of 1.11 micrometers and a standard deviation of 0.180 micrometers. The particle size distribution of this ciprofloxacin powder is given in Table I below, and is plotted as line 20 in FIG. 3.

When the EVA had completely melted, 6.176 grams (15.0 percent by weight) of this ciprofloxacin powder was added gradually to the mixer. The speed of the mixer was increased to 60 RPM for 10 minutes to produce a uniform dispersion of the ciprofloxacin powder in the EVA melt.

The mixer was turned off and the ciprofloxacin/EVA dispersion was removed from the mixer, transferred to a glass container and cooled to room temperature under ambient conditions to solidify into a solid, non-porous composite material of the invention.

Optical microscopy of this composite material of the invention showed the presence of a dispersed phase of undissolved ciprofloxacin particles. DSC determination of the phases present was not done, but it is believed that two solid solution phases of ciprofloxacin/EVA were formed here as in Example 1.

Example 5

40 grams of an EVA containing 32 wt. % vinyl acetate designated ELVAX™ 150 having a melt index of 43 g/10 min. as measured by ASTM D 1238 was charged to the mixing chamber of the same Brabender Plasticorder as described in Example 1 preheated to a temperature of 140° C. The EVA was melted at a mixing speed of 35 rpm under a flow of dry nitrogen.

When the EVA had completely melted, 1.237 grams (3.00 percent by weight) of the same ciprofloxacin powder as described in Example 4 was added gradually to the mixer. The speed of the mixer was increased to 50 RPM for 20 minutes to produce a uniform dispersion of the ciprofloxacin powder in the EVA melt.

The mixer was turned off and the ciprofloxacin/EVA dispersion was removed from the mixer, transferred to a glass container and cooled to room temperature under ambient conditions to solidify into a solid, non-porous composite material of the invention.

Optical microscopy of this composite material of the invention showed the presence of a dispersed phase of undissolved ciprofloxacin particles. DSC determination of the phases present was not done, but it is believed that two solid solution phases of ciprofloxacin/EVA were formed as in Example 1.

A control sample of this same EVA was prepared consisting of a 1.6 mm thick disk. The disk showed 0.20 percent by weight of dissolution in distilled water in 30 days at 35° C.

TABLE I

Particle Size Distributions of Ciprofloxacin

| d, Particle Size, um | Volume % Examples 1-3 | Volume % Examples 4-5 |
|---|---|---|
| 0.339 | | 0.12 |
| 0.388 | | 0.31 |
| 0.445 | | 0.71 |
| 0.509 | | 1.52 |
| 0.582 | | 3.05 |
| 0.668 | | 5.49 |
| 0.765 | | 8.57 |
| 0.877 | | 11.44 |
| 1.004 | 0.2 | 13.2 |
| 1.15 | 0.38 | 13.31 |
| 1.318 | 0.58 | 11.95 |
| 1.509 | 0.74 | 9.78 |
| 1.729 | 0.81 | 7.44 |
| 1.98 | 0.8 | 5.26 |
| 2.268 | 0.79 | 3.42 |
| 2.598 | 0.8 | 2.04 |
| 2.976 | 0.91 | 1.16 |
| 3.408 | 1.2 | 0.64 |
| 3.904 | 1.71 | 0.34 |
| 4.472 | 2.48 | |
| 5.122 | 3.44 | |
| 5.866 | 4.52 | |
| 6.719 | 5.61 | |
| 7.696 | 6.73 | |
| 8.815 | 7.73 | |
| 10.09 | 8.55 | |
| 11.56 | 9.26 | |
| 13.24 | 9.62 | |
| 15.17 | 9.33 | |
| 17.37 | 8.41 | |
| 19.9 | 6.72 | |
| 22.79 | 4.57 | |
| 26.11 | 2.54 | |
| 29.9 | 1.1 | |

Example 6

The composite material of the invention prepared in Example 2 was compression molded at a temperature of 175° C. into disks having dimensions of 0.16 cm thickness and 1.25 cm diameter. The initial weight of ciprofloxacin in the disks was known from the concentration of ciprofloxacin in the composite material and the measured weight of the disks. The disks were placed in sample vials with 15.0 ml of distilled water at 22° C.±2° C. Racks of vials were agitated. The distilled water was replaced at intervals of one day. The concentration, and from that, the weight of ciprofloxacin in the water was determined using a Beckman DU-530 UV-vis spectrophotomer. The cumulative weight of ciprofloxacin released was determined by summing the weights for each interval. The cumulative percent of the initial weight of the ciprofloxacin bioactive agent, ($M_t$) released from the disk into the water is given in Table II below and plotted as line 30 in FIG. 6. The measurements were terminated after 31 days.

Figure 7:
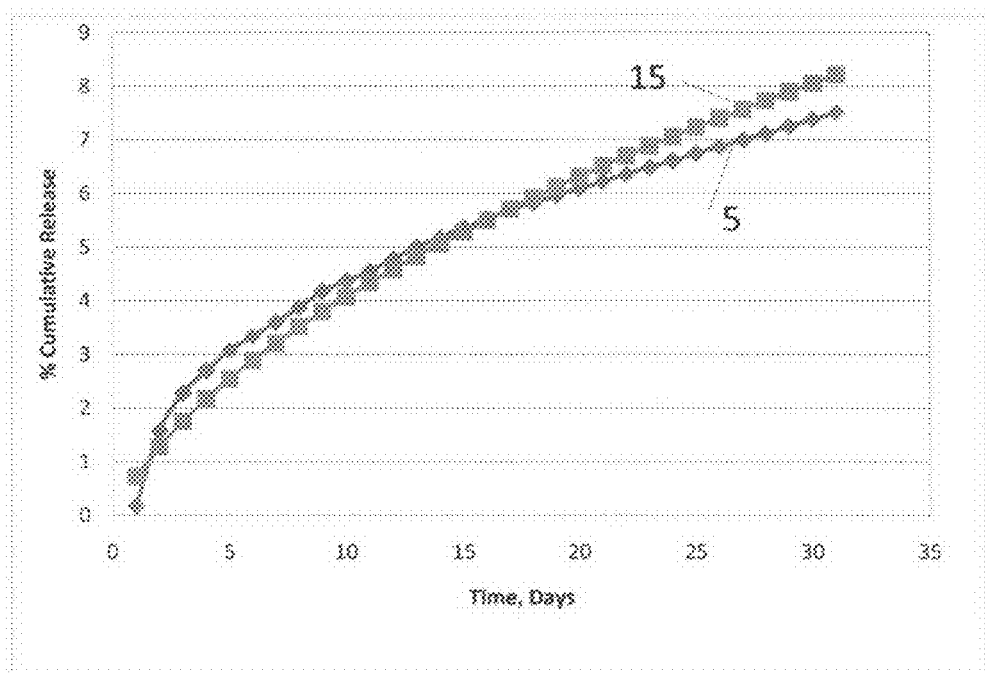
FIG. 7 is a plot of calculated and observed cumulative release of bioactive agent as a percentage of the initial bioactive content as a function of time for Example 6.

The cumulative percentage release of ciprofloxacin was described by Equation 2 below with a maximum deviation of less than 20% over the period from day 2 to day 30:

$$M_t = 1.8181\sqrt{1+0.95t} - 1.8181 \qquad \text{Eq. 2}$$

where: $M_t$ is the cumulative weight of bioactive agent released divided by the initial weight of bioactive agent weight×100;

t is time in days.

in FIG. 7. The observed cumulative percentage release of ciprofloxacin (5) is compared with that calculated (15) from Eq. 2

Surprisingly, it may be seen from Table II that the release of ciprofloxacin from the composite of the invention was essentially constant at 0.13±0.01% per day over the period from 18 to 31 days. The rate of change of release rate over this period was less than 0.05% per day per day. Extended, essentially constant, drug release was obtained over this period. Without being held to a particular explanation, it is believed that this useful drug release profile was related to the unique Weibull particle size distribution of the drug and/or the unique phase structure of the composite.

Example 7

The composite material of the invention prepared in Example 3 was compression molded at a temperature of 175° C. into disks having dimensions of 0.16 cm thickness and 1.25 cm diameter. The disks were weighed and placed in distilled water as in Example 2. The weight of ciprofloxacin extracted each day and the cumulative weight extracted was measured as in Example 2. The cumulative percent of the initial weight of the ciprofloxacin bioactive agent, (Mt) released from the disk into the water is given in Table ii below and plotted as line 40 in FIG. 6.

The cumulative percentage release of ciprofloxacin was described by Equation 3 below with a maximum deviation of less than 20% over the period from day 2 to day 30:

$$M_t = 3.2\sqrt{1+0.1t} - 3.2 \qquad \text{Eq. 3}$$

Where: $M_t$ is the cumulative weight of bioactive agent released divided by the initial weight of bioactive agent weight×100;

t is time in days.

Figure 8:
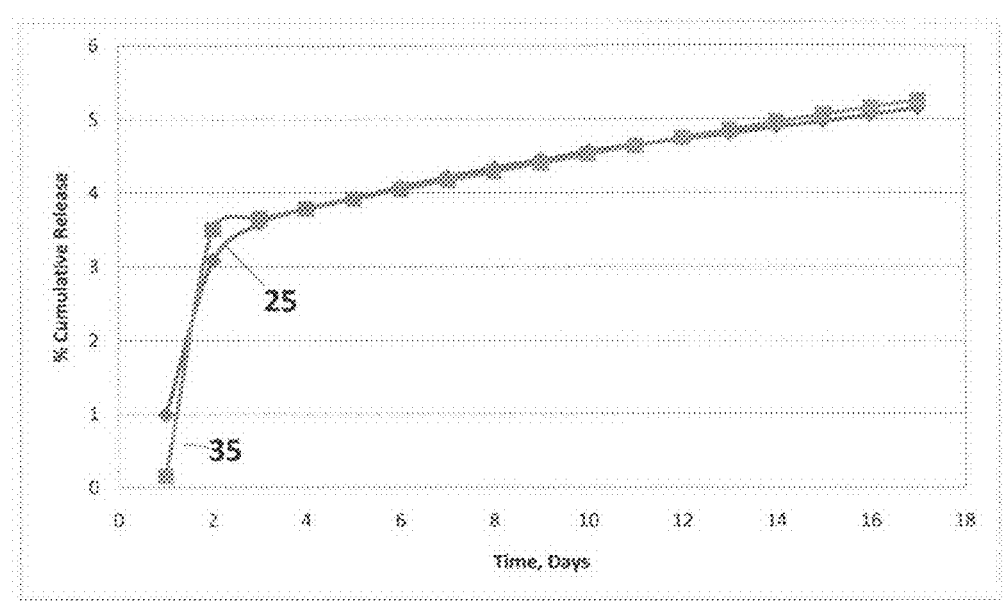
FIG. 8 is a plot of calculated and observed cumulative release of bioactive agent as a percentage of the initial bioactive content as a function of time for Example 7.

The observed (25) cumulative percentage release of ciprofloxacin is compared with that calculated (35) from Eq. 3 in FIG. 8. Surprisingly, it may be seen from Table II or from Eq. 3 that the rate of release of ciprofloxacin from the composite of the invention was essentially constant at 0.08±0.01% per day over the period from 11 to 17 days. Extended, essentially constant, drug release was obtained over this period.

Example 8

The material prepared in Example 4 was compression molded at a temperature of 175° C. into disks having dimensions of 0.16 cm thickness and 1.25 cm diameter. The disks were weighed and placed in distilled water as in Example 2. The weight of ciprofloxacin extracted each day and the cumulative weight extracted was measured as in Example 2. The concentration, and from that, the weight of ciprofloxacin in the water was determined using a Beckman DU-530 UV-vis spectrophotomer. The cumulative weight of ciprofloxacin released was determined by summing the weights for each interval. The cumulative percent of the initial weight of the ciprofloxacin bioactive agent released from the disk into the water is given in Table II below and is plotted as line 50 in FIG. 6.

Figure 6:
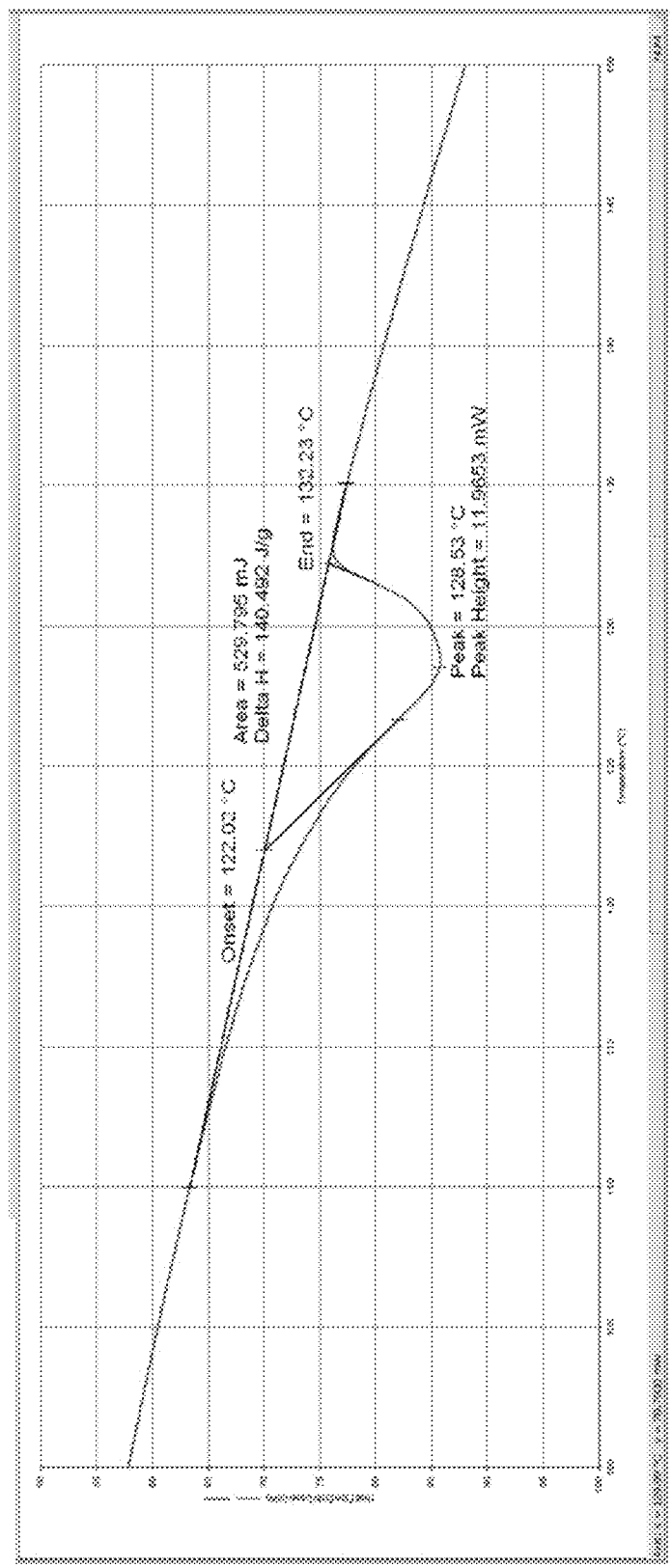
FIG. 6 is a plot of cumulative release of bioactive agent as a percentage of the initial bioactive content as a function of time for Examples 6- to 9.

Surprisingly, it will be seen from Table II or FIG. 6 that in comparison to Example 2, the cumulative releases of bioactive agent were more than an order of magnitude lower in this example containing 2.5 to 5 fold higher bioactive concentration, but where the bioactive agent had a log normal particle size distribution.

Example 9

The material prepared in Example 5 was compression molded at a temperature of 175° C. into disks having dimensions of 0.16 cm thickness and 1.25 cm diameter. The disks were weighed and placed in distilled water as in Example 2. The weight of ciprofloxacin extracted each day and the cumulative weight extracted was measured as in Example 2. The concentration, and from that, the weight of ciprofloxacin in the water was determined using a Beckman DU-530 UV-vis spectrophotomer. The cumulative weight of ciprofloxacin released was determined by summing the weights for each interval. The cumulative percent of the initial weight of the ciprofloxacin bioactive agent released from the disk into the water is given in Table II below and is plotted as line 60 in FIG. 6. For clarity, the designation 18 wt. % VA/EVA refers to an ethylene-vinyl acetate copolymer (EVA) containing 18 wt. % vinyl acetate (VA).

TABLE II

| | $M_t$, Cumulative % of Initial Ciprofloxacin Released | | | |
|---|---|---|---|---|
| | Example 6 3 wt. % ciprofloxacin 18 wt. % VA/EVA Weibull Particle Dist. | Example 7 6 wt. % ciprofloxacin 18 wt. % VA/EVA Weibull Particle Dist. | Example 8 15 wt. % ciprofloxacin 18 wt. % VA/EVA Log Normal Particle Dist. | Example 9 3 wt. % ciprofloxacin 32 wt. % VA/EVA Log Normal Particle Dist. |
| 1 | 0.176 | 0.99 | 0.098 | 0.058 |
| 2 | 1.58 | 3.08 | 0.14 | 0.15 |
| 3 | 2.28 | 3.58 | 0.15 | 0.2 |
| 4 | 2.7 | 3.79 | 0.16 | 0.24 |
| 5 | 3.08 | 3.93 | 0.17 | 0.26 |
| 6 | 3.34 | 4.08 | 0.17 | 0.28 |
| 7 | 3.6 | 4.22 | 0.17 | 0.29 |
| 8 | 3.88 | 4.35 | 0.17 | 0.32 |
| 9 | 4.18 | 4.45 | 0.17 | 0.35 |
| 10 | 4.37 | 4.57 | 0.17 | 0.37 |
| 11 | 4.56 | 4.65 | 0.17 | 0.39 |
| 12 | 4.78 | 4.73 | 0.17 | 0.41 |
| 13 | 5 | 4.8 | 0.17 | 0.42 |
| 14 | 5.18 | 4.89 | 0.17 | 0.44 |
| 15 | 5.36 | 4.97 | 0.17 | 0.46 |
| 16 | 5.52 | 5.06 | 0.17 | 0.47 |
| 17 | 5.7 | 5.15 | 0.17 | 0.48 |
| 18 | 5.82 | In process | 0.17 | 0.49 |
| 19 | 5.96 | | 0.17 | 0.51 |
| 20 | 6.08 | | 0.17 | 0.52 |
| 21 | 6.22 | | 0.17 | 0.53 |
| 22 | 6.35 | | 0.17 | 0.54 |
| 23 | 6.48 | | 0.17 | 0.56 |
| 24 | 6.6 | | 0.17 | 0.57 |
| 25 | 6.74 | | 0.17 | 0.58 |
| 26 | 6.86 | | 0.17 | 0.59 |
| 27 | 7 | | 0.17 | 0.6 |
| 28 | 7.12 | | 0.17 | 0.62 |
| 29 | 7.25 | | 0.17 | 0.62 |
| 30 | 7.38 | | 0.17 | 0.62 |
| 31 | 7.51 | | 0.17 | 0.62 |

Example 10

A solid non-porous composite material of the invention was prepared as in Example 1 consisting of 81 percent by weight of the same ELVAX™ 560 EVA, 3 percent by weight of the same ciprofloxacin powder as in Example 1, 3 percent by weight of usnic acid (C.A.S. Registry No. 7562-61-0), and 3 percent by weight of polyhexamethylene biguanide hydrochloride (C.A.S. Registry No. 57028-96-3). Usnic acid and polyhexamethylene biguanide hydrochloride are anti-bacterial compounds.

This composite of the invention was molded into 6 mm diameter circular coupons. The coupons of each kind were placed on four Petri dishes containing LB broth, each freshly inoculated with a culture of one of: *Haemophilus influenza, Streptococcus pneumonia, Pseudomonas aeruginosa*, or *Staphylococcus aureus*, respectively. The cultures were incubated at a temperature of 37° C. to allow the bacteria to grow. At the end of five days. it was found that bacterial growth had been inhibited in zones measuring 7.5 mm, 4.5 mm, 7 mm, and 4.5 mm around the coupons respectively for the four organisms.

Example 11

25.2 grams of an EVA containing 32 wt. % vinyl acetate designated ELVAX™ 150 and 8.4 grams of polyethylene glycol (PEG) were charged to the mixing chamber of the same Brabender Plasticorder as described in Example 1 preheated to a temperature of 140° C. The PEG from Sigma-Aldrich had a molecular weight of 8000 Daltons. The EVA and polyethylene glycol were melted at a mixing speed of 35 rpm under a flow of dry nitrogen.

When the EVA and PEG had completely melted, 8.4 grams (20 percent by weight) of the same ciprofloxacin powder as described in Example 1 was added gradually to the mixer. The speed of the mixer was increased to 50 RPM for 20 minutes to produce a uniform dispersion of the ciprofloxacin powder in the EVA and PEG melt.

The mixer was turned off and the ciprofloxacin/polymer dispersion was removed from the mixer, transferred to a glass container and cooled to room temperature under ambient conditions to solidify into solid, non-porous composite material of the invention.

Optical microscopy of this composite material of the invention showed the presence of a dispersed phase of ciprofloxacin particles. While differential scanning calorimetry was not performed on this composite, it is believed that two solid solution phases of ciprofloaxacin/EVA and EVA/ciprofloxacin were present here as in the composite of Example 1.

A control sample was prepared consisting only of the same EVA and PEG in the same proportions as above but without any ciprofloxacin. A 1.6 mm thick disk of this material showed 0.26 percent by weight of dissolution in distilled water at 35° C. in 30 days.

Example 12

The composites of the invention described in Examples 1 to 5 and 11 were molded into 6 mm diameter circular coupons. Blank control coupons containing no bioactive material were also molded. The coupons of each kind were placed on from two to six Petri dishes containing LB broth, each freshly inoculated with a culture of one of *Pseudomonas aeruginosa*, PAO1 Xen#41, or methicillin-resistant *Staphylococcus aureus* Xen#31 respectively. The cultures were incubated twenty-four hours at a temperature of 37° C. to allow the bacteria to grow. Measurements were made of the diameter of a circular zone of growth inhibition surrounding each coupon where no bacteria grew. The mean diameter, standard deviation and number of samples tested are presented in Table III below.

TABLE III

| | Zone of Inhibition | | | | | |
|---|---|---|---|---|---|---|
| | P. aeruginosa, | | | methicillin-resistant S. aureus | | |
| | Mean, mm | Std. Dev. | n | Mean, mm | Std. Dev. | n |
| Blank Control, 18 wt. % VA/EVA | 0 | — | 3 | 0 | — | 3 |
| Blank Control, 32 wt. % VA/EVA | 0 | — | 3 | 0 | — | 3 |
| Example 1 Composite, 15 wt. % ciprofloxacin Weibull Dist. 18 wt. % VA/EVA | 25.1 | 1.7 | 6 | 0 | — | 3 |
| Example 2 Composite 3 wt. % ciprofloxacin Weibull Dist 18 wt. % VA/EVA | 19.2 | 1.5 | 6 | 0 | — | 6 |
| Example 3 Composite 6 wt. % ciprofloxacitn Weibull Dist 18 wt. % VA/EVA | 28.0 | 3.3 | 2 | 5.85 | 0.92 | 2 |
| Example 4 Composite 15 wt. % ciprofloxacin Log Normal Dist. 18 wt. % VA/EVA | 20.1 | 3.8 | 6 | 0 | — | 3 |
| Example 5 Composite 3 wt. % ciprofloxacin Log Normal Dist. 32 wt. % VA/EVA | 11.0 | 4.9 | 6 | 0 | — | 6 |
| Example 11 Composite 20 wt. % ciprofloxacin Weibull Dist. 60 wt. % EVA(32 wt. % VA/EVA), 20 wt. % PEG | 28.8 | 0.1 | 2 | 5.45 | 0.21 | 2 |

Example 14

The material prepared in Example 11 containing 20 wt. % ciprofloxacin was compression molded at a temperature of 175° C. into disks.

A cytotoxicity assay was run using fibroblasts derived from rabbit skin. Yellow MIT (3-(4,5-dimethylthiazol-2-yl)-2,5-diphenyltetrazolium bromide) was used to determine the cytotoxicity effect of the material of the invention. In this assay, MIT is reduced to purple formazan by metabolically active cells, and the purple formazan is measured by a spectrophotometer. This is widely accepted as a reliable way to examine cell proliferation which directly correlates with the level of cytotoxicity.

Fibroblasts grown to confluence in 100 cm plates were subcultured on 12-well plates and left undisturbed for 24 hours. After 24 hours, fibroblast cells were treated or untreated by the disks. The disks were incubated in the fibroblast for 24 hours followed by the addition of MIT and incubated for 3 hours at 37° C. After 3 hours, the resultant purple formazin was solubilized, incubated in the dark for 2 hours and quantified using a spectrophotometer at 595 nM.

No significant difference was seen between the absorbance values between treated and non-treated cellular populations. The results signify that cellular proliferation potential was not affected by the incubation of cells with the disks made from the material of the invention

Example 15

A test was devised to assess the ability of a composite of the invention to kill bacteria in a surrounding fluid, and to prevent biofilm formation. The test, involving multiple challenges by an infectious biofilm forming bacteria, is regarded as very severe.

The composite prepared in Example 5 was compression molded into disks having a mass of 9.7±0.7 mg. approximating the mass of pediatric ear tubes. The disks contained 3 percent by weight of ciprofloxacin with a log normal particle size distribution uniformly dispersed in a 32 wt. % VA/EVA. Positive control disks consisting only of the same EVA, but no ciprofloxacin were also molded.

Bacteria inoculated nutrient medium was contained in the wells of a 96 well MBEC AssaySystem (BioSurface Technologies, Bozeman, Mont.) two plate assembly. The disks formed of the composite of the invention and also the control disks were fixed on polystyrene pegs attached to the top plate. Some parts of the top plate had no disks of either type attached as a negative control. Upon assembling the top plate onto the bottom plate each disk was immersed into one of the wells containing 100 μL of rich medium (brain heart infusion broth) having $1\times10^5$ per mL of live bacteria ($1\times10^4$ bacteria per disk).

The species of bacteria used was *Pseudomonas aeruginosa*: a biofilm forming pathogen commonly found in ear tube infections (post-tympanostomy tube otorhea). A genetically bioluminescent strain, *P. aeruginosa* Xen 4, was used to assist in monitoring the growth of the bacteria in the medium surrounding the disk (plantonic growth) and on the disk itself (biofilm growth). The bacteria were incubated at 37° C., 5% $CO_2$ with 50 rpm orbital shaking.

After a 24 hour growth period, the top plate was removed from the assembly. The bottom plate containing the medium and plantonic bacteria was quantified for bioluminescence. The light emitted by the bacteria was measured using an IVIS™ Imaging System from Caliper Life Sciences, Hopkinton, Mass. Light emission was proportional to the quantity of active bacteria. Growth of bacteria in the fluid was also measured by the conventional method of optical density using a wavelength of 595 nM. Higher bacterial count causes more light to be blocked, and therefore higher optical density ($OD_{595}$).

The top plate with the attached disks was rinsed in buffer to remove loosely adhered cells and placed in a new bottom plate containing fresh medium with another challenge of $1\times10^5$ CFU/ml bacteria freshly grown from an overnight culture. The MBEC plate was then quantified for a bioluminescence signal. Since the fresh inoculums consisted of too few bacteria to produce a detectable signal, and the previous planktonic bacteria had been removed, the only source of the signal was from biofilm bacteria attached to the disk and possibly to the polystyrene peg.

Measurements and re-Immersion in fresh medium was repeated five times per week.

Figure 9:
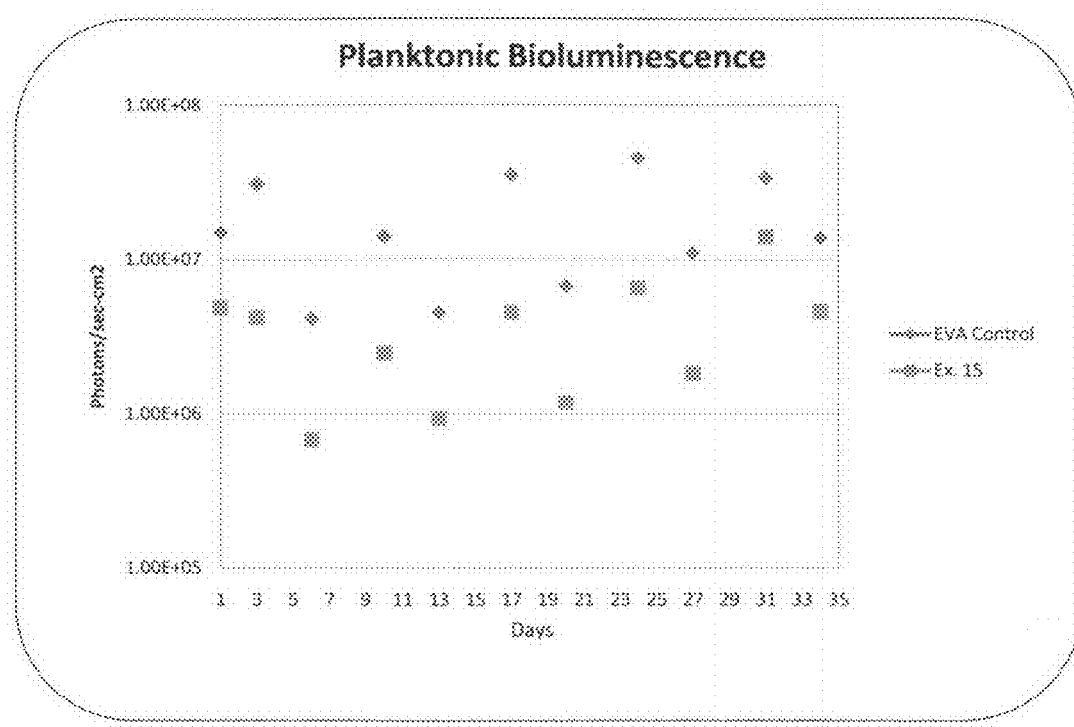
FIG. 9 is a plot of planktonic bioluminescence as a function of time for Example 15.

The measurements of bioluminescence of planktonic bacteria are presented in Table IV below and are plotted in FIG. 9. In FIG. 9, the squares are measurements for the wells that had disks formed of the composite of the invention. The diamonds are measurements for wells containing the disks formed of the control EVA.

TABLE IV

Bioluminescence of Planktonic Bacteria in 100 μL
Avg Radiance
(photons/sec/cm2)
(mean values, n = 4 disks)

| Day | Control 32 wt. % VA/EVA | 3 wt. % ciprofloxacin, log normal distribution in 32 wt. % VA/EVA |
|---|---|---|
| 1 | 1.50E+07 | 4.88E+06 |
| 3 | 3.09E+07 | 4.22E+06 |
| 6 | 4.15E+06 | 6.76E+05 |
| 10 | 1.41E+07 | 2.47E+06 |
| 13 | 4.49E+06 | 9.26E+05 |
| 17 | 3.53E+07 | 4.52E+06 |
| 20 | 6.73E+06 | 1.18E+06 |
| 24 | 4.57E+07 | 6.54E+06 |
| 27 | 1.11E+07 | 1.83E+06 |
| 31 | 3.40E+07 | 1.40E+07 |
| 34 | 1.37E+07 | 4.59E+06 |
| 35 | 3.29E+07 | 2.25E+07 |

Figure 10:
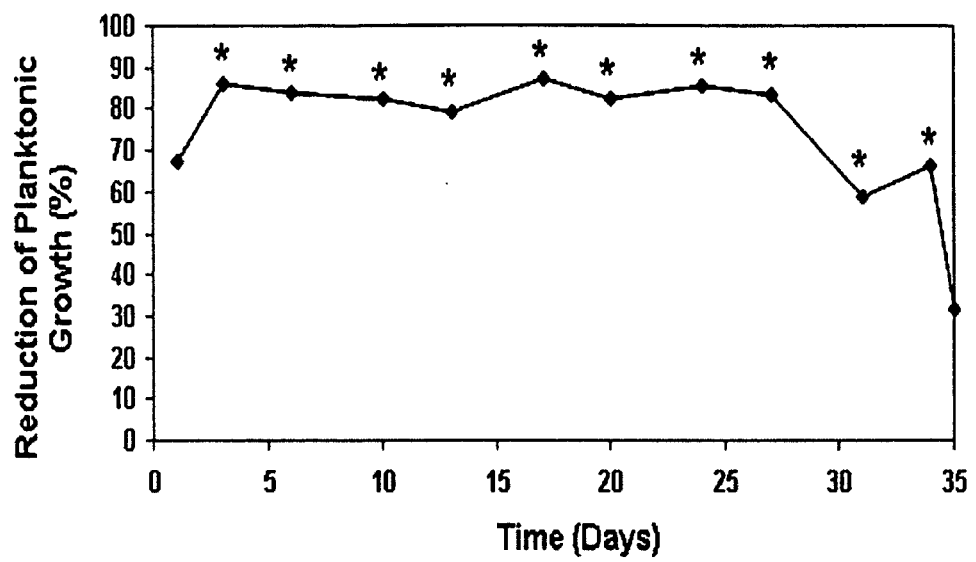
FIG. 10 is a plot of reduction in planktonic bacterial growth as measured by bioluminescence compared to the control as a function of time for Example 15.

The reduction of planktonic growth was determined from the bioluminescence measurements of the wells. Planktonic growth in the presence of disks formed of a composite of the invention is compared with that in the presence of control disks in FIG. 10. Statistically significant reductions as determined by a 2 tail Wtest are indicated by "*". The disks formed of a composite of the invention caused a reduction in planktonic growth in the fluid of between 65 and 90% up to day 27. The reductions were statistically significant between days 2 and 34.

Figure 11:
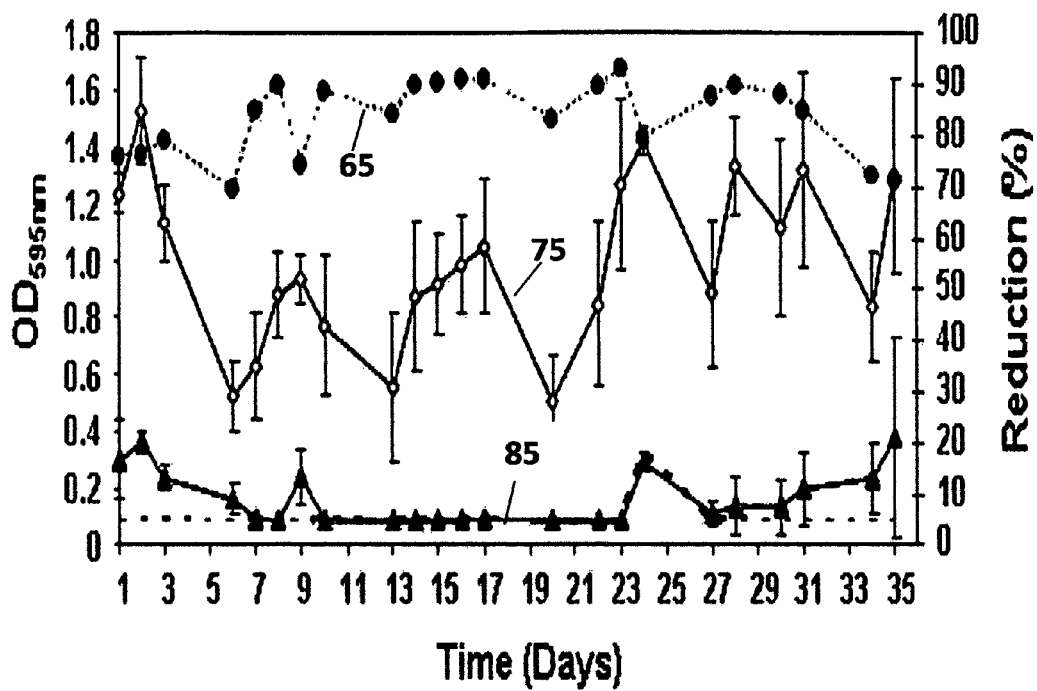
FIG. 11 is a plot of optical density and reduction in planktonic growth as measured by optical density compared to the control as a function of time for Example 15.

The measurements of optical density are presented in Table V below and are plotted in FIG. 11.

TABLE V

Optical Density of Planktonic Bacteria in 100 μL
Optical Density (595 nm)

| | (−)control | | (+)Control 32 wt. % VA/EVA | | 3 wt. % ciprofloxacin, log normal distribution in 32 wt. % VA/EVA | |
|---|---|---|---|---|---|---|
| Day | mean | stdev | mean | stdev | mean | stdev |
| 1 | 0.186 | 0.108 | 1.235 | 0.390 | 0.298 | 0.139 |
| 2 | 0.139 | 0.060 | 1.528 | 0.195 | 0.362 | 0.035 |
| 3 | 0.136 | 0.069 | 1.136 | 0.253 | 0.236 | 0.041 |
| 6 | 0.186 | 0.174 | 0.525 | 0.205 | 0.160 | 0.056 |
| 7 | 0.729 | 0.582 | 0.631 | 0.160 | 0.095 | 0.005 |
| 8 | 0.545 | 0.454 | 0.881 | 0.273 | 0.088 | 0.004 |
| 9 | 0.637 | 0.475 | 0.935 | 0.254 | 0.241 | 0.099 |
| 10 | 0.490 | 0.399 | 0.773 | 0.373 | 0.088 | 0.002 |
| 13 | 0.426 | 0.355 | 0.555 | 0.156 | 0.088 | 0.004 |
| 14 | 0.430 | 0.368 | 0.874 | 0.364 | 0.088 | 0.004 |
| 15 | 0.622 | 0.516 | 0.919 | 0.459 | 0.087 | 0.003 |
| 16 | 0.737 | 0.589 | 0.985 | 0.386 | 0.087 | 0.002 |
| 17 | 0.664 | 0.500 | 1.050 | 0.240 | 0.093 | 0.003 |
| 20 | 0.549 | 0.516 | 0.508 | 0.303 | 0.085 | 0.003 |
| 22 | 0.447 | 0.330 | 0.846 | 0.372 | 0.086 | 0.006 |
| 23 | 0.606 | 0.470 | 1.264 | 0.165 | 0.085 | 0.004 |
| 24 | 0.303 | 0.031 | 1.421 | 0.056 | 0.292 | 0.035 |
| 27 | 0.493 | 0.409 | 0.885 | 0.419 | 0.109 | 0.048 |
| 28 | 0.711 | 0.546 | 1.332 | 0.020 | 0.135 | 0.097 |
| 30 | 0.639 | 0.522 | 1.114 | 0.408 | 0.134 | 0.096 |
| 31 | 0.624 | 0.481 | 1.320 | 0.112 | 0.198 | 0.130 |
| 34 | 0.401 | 0.274 | 0.838 | 0.372 | 0.233 | 0.123 |
| 35 | 0.711 | 0.558 | 1.301 | 0.314 | 0.375 | 0.353 |

Optical density is a standard measure of the amount of bacterial growth in the fluid. In FIG. 11 line 85 represents measurements for the wells that had disks formed of the composite of the invention. Line 75 represents measurements for the wells that had disks formed of the EVA not containing ciprofloxacin. Error bars are 95% confidence limits calculated from data for 4 replicate disks.

The disks formed of the composite of the invention held planktonic growth at, or near zero in the fluid for the first 31 days. Planktonic growth was significantly less for wells containing a disk formed of the composite of the invention than for wells containing a disk formed of the control EVA. The percent reduction in optical density is shown in FIG. 11 as line 65 with reference to the right hand Y axis. The percent reduction in optical density ranged from 70 to 90%.

Figure 12:
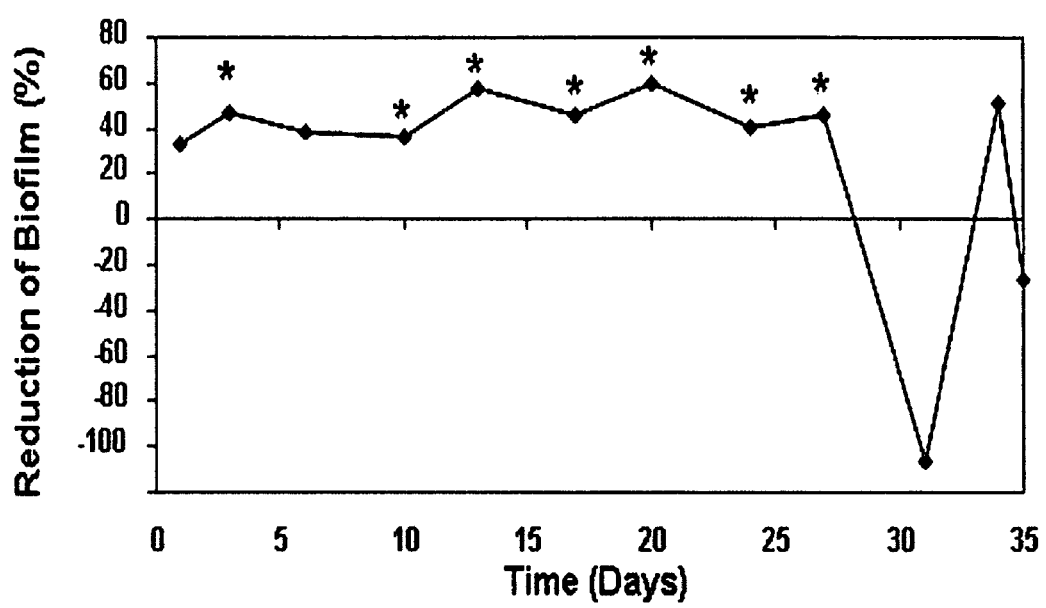
FIG. 12 is a plot of reduction in biofilm formation as a function of time for Example 15.
Figure 1:
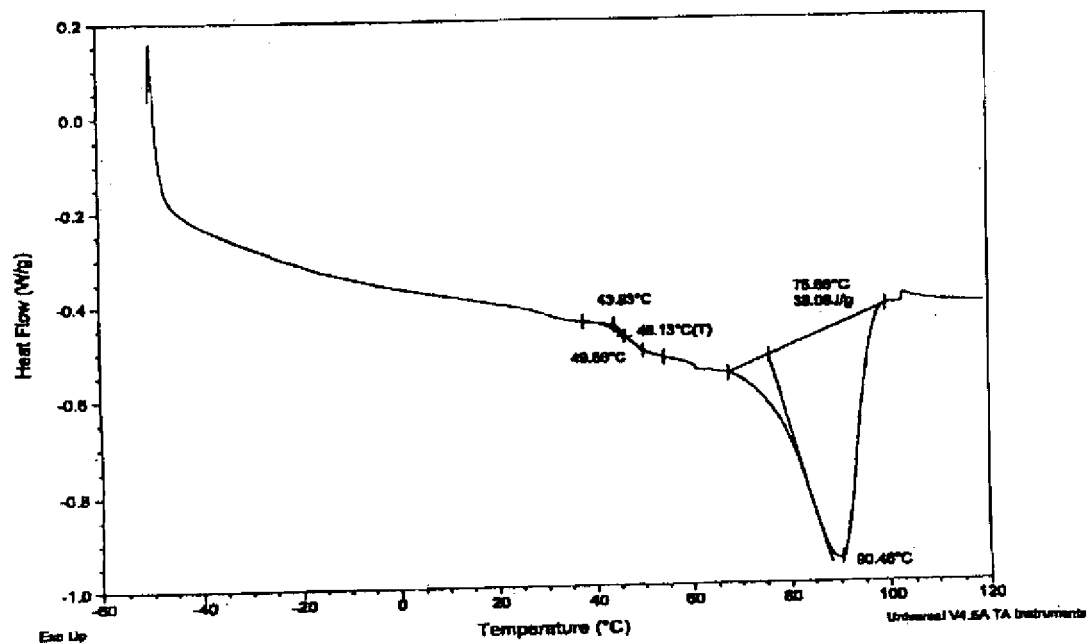
Figure 2:
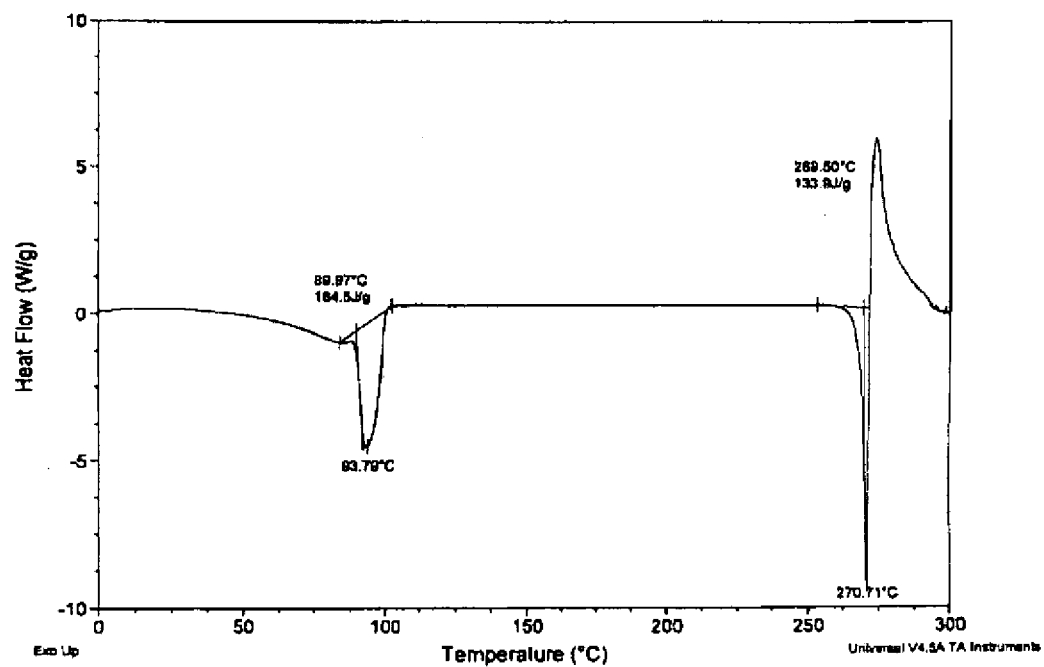
Figure 3:
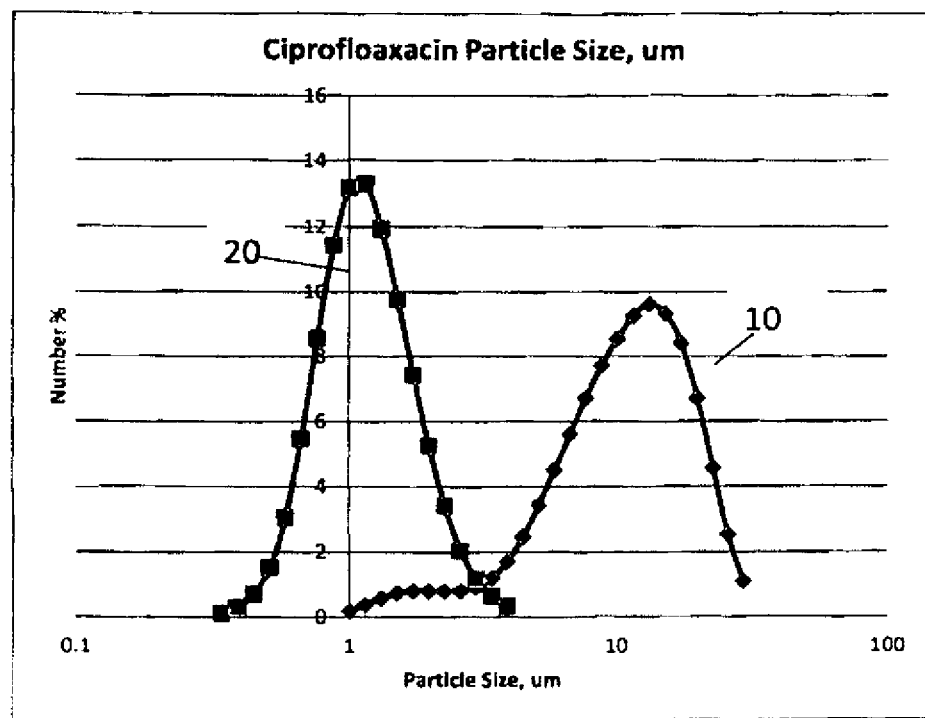
Figure 4:
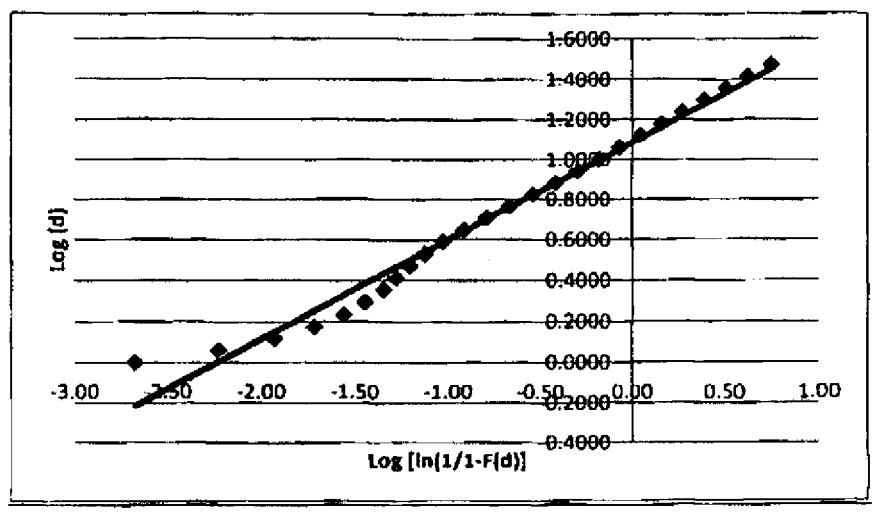
Figure 5:
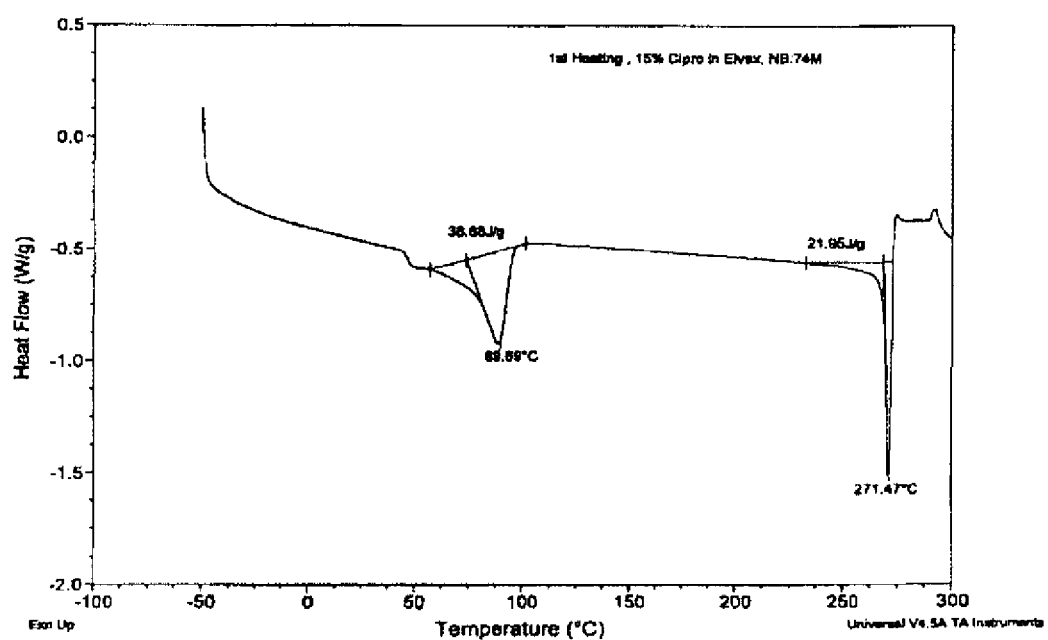

Percent reduction in biofilm formation on the disks formed from the composite of the invention compared to the control disks is shown in FIG. 12. Between days 2 and 27 the amount of the biofilm was reduced by approximately 50%. Statistically significant reductions as determined by the 2 tail t-test are indicated by the "*". At failure, the planktonic bacteria in the challenge medium survived and had formed biofilms on the surfaces of the depleted disks.

Example 16

In this example, the volume of medium was increased from 100 μL to 500 μL using a 48 well MBEC plate to more closely approximate the expected volume of effusion during an episode of chonic otitis media with infusion. Disks of the same weight as used in Example 15 consisting of composites of the invention, and also control disks containing no antibiotic, were placed directly into the 500 μL wells. The same concentration of *P. aeruginosa* Xen 4 was used so that the total challenge per disk was increased by a factor of 5 to $5 \times 10^4$ bacteria per disk. The medium in each well was replaced daily and optical density ($OD_{595}$) was measured.

The measurements of optical density are presented in Table VI below and are plotted in FIG. 13.

TABLE VI

Optical Density of Planktonic Bacteria in 500 μL

In FIG. 13

| Day | Line 41 (+)Control 32 wt. % VA/EVA | Line 31 3 wt. % ciprofloxacin, log normal distribution in 32 wt. % VA/EVA | Line 21 3 wt. % ciprofloxacin, Weibull distribution in 18 wt. % VA/EVA | Line 11 20 wt. % ciprofloxacin Weibull Dist. 60 wt. % EVA(32 wt. % VA/EVA), 20 wt. % PEG |
|---|---|---|---|---|
| 1 | 1.850 | 0.039 | 0.089 | −0.107 |
| 2 | 1.540 | 0.094 | 0.145 | 0.067 |
| 3 | 1.718 | 0.139 | 0.058 | 0.127 |
| 4 | 1.786 | 0.865 | 0.081 | 0.009 |
| 5 | 1.721 | 1.079 | 0.625 | 0.006 |
| 6 | 1.782 | 0.823 | 0.841 | 0.005 |
| 7 | 1.566 | 1.082 | 0.821 | 0.205 |
| 8 | | | | In progress |

Having thus described the invention in rather full detail, it will be understood that such detail need not be strictly adhered to but that further changes and modifications may suggest themselves to one skilled in the art, all falling within the scope of the invention as defined by the subjoined claims.

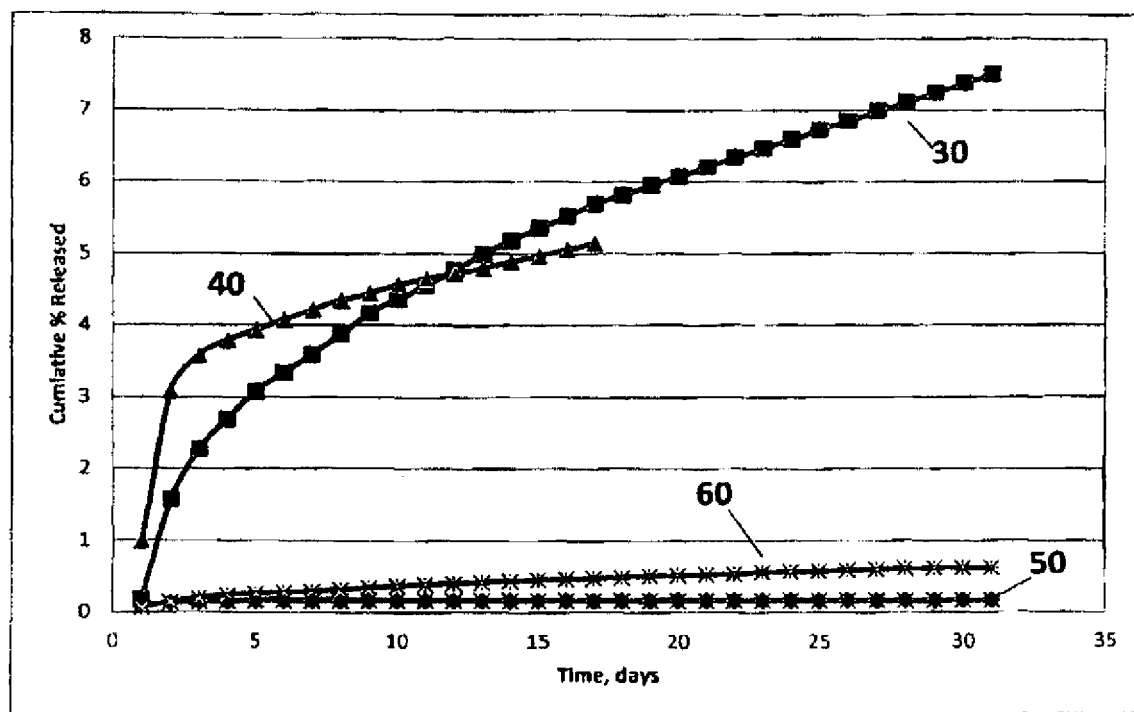

What is claimed is:

1. A solid, non-porous composite comprised of:
a) a) a non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 35° C. in 30 days; said thermoplastic polymer material being comprised of a melt blend of:
(i) an ethylene-vinyl acetate copolymer having a melt index less than about 50 g/10 min. as measured by ASTM D1238 and comprising 10 to 50 percent by weight of vinyl acetate, (ii) polyethylene glycol having a weight average molecular weight of tom about 2,000 to about 20,000 Daltons; and
b) one or more bioactive agents comprising at least ciprofloxacin antibiotic dispersed uniformly throughout said polymer material; said bioactive agents comprising about 1 to about 60 percent by weight of said polymer plus bioactive agents;
wherein at least one said bioactive agent has less than about 5 percent weight loss at a temperature of 200° C. when measured in a pure state by thermogravimetric analysis at a heating rate of 10° C./min; and,
wherein said ciprofloxacin is present in said polymer material as:
i) a solid solution phase with said polymer material comprised of from about 0.1 to about 30 percent by weight of said ciprofloxacin; and
ii) a solid solution phase with said polymer material comprised of from about 95 to about 99.99 percent by weight of said ciprofloxacin; and
iii) a phase selected from a supersaturated solution, essentially pure, ciprofloxacin, a solid solution comprised of, ciprofloxacin and their combination.

2. A solid, non-porous composite comprised of:
a) a non-biodegradable thermoplastic polymer material melt-processable at a temperature not exceeding 260° C., said polymer material suitable for implantation in a living mammal, a 1.6 mm thick disk of said polymer material having less than about one percent by weight dissolution in distilled water at 37° C. in 30 days; said thermoplastic polymer material being comprised of a melt blend of:
(i) an ethylene-vinyl acetate copolymer having a melt index less 50 g/110 min. as measured by ASTM D1238 and comprising 10 to 50 percent by weight of vinyl acetate;
(ii) polyethylene glycol having a weight average molecular weight of trom about 2,000 to about 20.000 Daltons; and
b) one or more bioactive agents comprising at least ciprofloxacin antibiotic dispersed uniformly throughout said polymer material; said bioactive agents comprising about 1 to about 60 percent by weight of said polymer plus bioactive agents; said ciprofloxacin, before dispersion in said thermoplastic material, having a particle size distribution as measured by Horiba Instruments, Inc. Model LA-900 Laser Scattering Particle Size Distribution Analyzer best described b a Weibull function with an index of determination of at least about 0.90, said distribution having a characteristic size of from about 5 to about 100;
wherein at least one said bioactive agent has less than about 5 percent weight loss at a temperature of 200°

C. when measured in a pure state by thermogravimetric analysis at a heating rate of 10° C./min; and,
wherein said bioactive agent is present in said polymer material as:
i) a solid solution phase with said polymer material comprised of from about 0.1 to about 30 percent by weight of said ciprofloxacin; and
ii) a solid solution phase with said polymer material comprised of from about 95 to about 99.99 percent by weight of said ciprofloxacin; and
iii) a phase selected from a supersaturated solution, essentially pure ciprofloxacin, a solid solution comprised of ciprofloxacin, and their combination.

3. The solid, non-porous composite of claim 1 or 2 wherein said ciprofloxacin has a particle size distribution best described by a Weibull function with an index of determination of at least about 0.94.

4. The solid, non-porous composition of claim 1 or 2 wherein said bioactive agent further includes a solid antibiotic.

5. The solid, non-porous composite of claim 4 wherein said antibiotic is selected from the group consisting of carbapenems, cephalosporins, penicillins, lincosamides, tetracyclins, macrolides, glycopeptides, quinolones, oxazolidinones, aminoclycosides, gyrase inhibitors, and their combination.

6. The solid, non-porous composite of claim 5 wherein said antibiotic is selected from the group consisting of beta lactam, meropenem, ceftazidime, amoxicillin, clindamycin, tetracycline, erythromycin, vancomycin, ciprofloxacin, ciprofloxacin hydrochloride linezolid, usnic acid, sodium usnate, polyhexamethylene biguanide, and their combination.

7. The composite of claims 1 or 2 wherein said composite when molded into a disk having dimensions of 0.16 cm thickness and 1.25 cm diameter, said disk having been placed in 15 ml of agitated distilled water at 22±2° C. and said water having been replaced with fresh distilled water at intervals, the cumulative percentage of the initial weight of bioactive agent released from the disk into the water over a period from day 2 to day 30 is given by the following equation with a maximum deviation less than 20% between the equation and measurements:

$$M_t = a\sqrt{1+bt} - a.$$

where: $M_t$ is the cumulative weight of bioactive agent released divided by the initial weight of bioactive agent weight×100;
t is time, days
a is from about 0.1 to about 5; and
b is from about 0.05 to about 5.

8. The solid, non-porous composite of claims 1 or 2, wherein said composite when molded into a disk having dimensions of 0.16 cm thickness and 1.25 cm diameter, said disk having been placed in 15 ml of agitated distilled water at 22±2° C. and said water having been replaced with fresh distilled water at intervals, the rate of change of the release rate is less than 0.05 percent per day per day over a period from at least about day 18 to at least about day 31.

9. The solid, non-porous composite of claims 1 or 2 containing less than about 25 percent by weight of materials commonly used in polymers selected from the group consisting of plasticizers, colorants, anti-oxidants, stabilizers, inert fillers, and their combination.

10. The solid, non-porous composite of claims 1 or 2 wherein said ethylene-vinyl acetate copolymer contains from about 15 to about 35 percent by weight of vinyl acetate.

11. The solid, non-porous composition of claim 1 or 2 wherein said non-porous composition is a tympanostomy tube.

12. The solid, non-porous composite of claims 1 or 2 useful in a device protective against colonization by organisms selected from the genera consisting of *Corynebacterium, Enterococcus, Escherichia, Haemophilus, Mycoplasma, Neisseria, Pseudomonas, Staphlococcus, Streptococcus, Campylobacter, Propionobacterium, Klebsiella, Enterobacter, Bacillus, Burkholderia, Mycobacterium, Clostridium, Legionella, Listeria, Salmonella, Vibrio, Candida*, and their combination.

13. The solid, non-porous composite of claims 1 or 2 said composite being molded into 6 mm diameter circular coupons, said coupons placed on four Petri dishes containing LB broth, said Petri dishes inoculated with a culture of *Haemophilus influenza, Streptococcus pneumonia, Pseudomonas aeruginosa* or *Staphylococcus aureus* respectively, wherein at 37° C. for 5 days, bacterial growth is inhibited in zones measuring at least 7.5 mm, 4.5 mm, 7 mm, and 4.5 mm around said coupons respectively for the four organisms.

14. An article comprising a composite of claim 7 said article being selected from the group consisting of tympanostomy tubes, central venous catheters, venous access devices, urinary catheters, dialysis catheters, peripheral IV catheters, ventricular shunts and drains, total parenteral nutrition lines, Tenckhoff catheters, Hickman/Broviak catheters, orthopedic implants, cochlear implants, dental implants, pacemaker leads, sutures, meshes, and stents.

15. An article according to claim 14 wherein said article has at least about 40% reduction in biofilm formation for at least 27 days compared to a control not containing an antibiotic.

16. An article according to claim 14 wherein said article has at least 50% reduction in bacterial growth in a fluid in contact with said article over a period of at least about 30 days.

17. An article according to claim 14 having no significant cytotoxicity for fibroblasts derived from rabbit skin as measured by a (3-(4,5-dimethylthiazol-2-yl)-2,5-diphenyltetrazolium bromide]assay.

* * * * *

UNITED STATES PATENT AND TRADEMARK OFFICE
CERTIFICATE OF CORRECTION

PATENT NO.         : 8,747,883 B2
APPLICATION NO.    : 12/802207
DATED              : June 10, 2014
INVENTOR(S)        : Mohamed E. Labib Page 1 of 7

It is certified that error appears in the above-identified patent and that said Letters Patent is hereby corrected as shown below:

In the drawing sheets, consisting of Figs. 1-6, should be deleted to be replaced with the drawing sheets, consisting of Figs. 1-6, as shown on the attached pages.

Signed and Sealed this
Seventh Day of October, 2014

Michelle K. Lee
*Deputy Director of the United States Patent and Trademark Office*